US011225690B2

(12) United States Patent
Lindley

(10) Patent No.: US 11,225,690 B2
(45) Date of Patent: Jan. 18, 2022

(54) METHODS OF DETECTING CANCER RECURRENCE

(71) Applicant: GMDx Co Pty Ltd., Melbourne (AU)

(72) Inventor: Robyn Lindley, Melbourne (AU)

(73) Assignee: GMDx Co Pty Ltd, Melbourne (AU)

( * ) Notice: Subject to any disclaimer, the term of this patent is extended or adjusted under 35 U.S.C. 154(b) by 800 days.

(21) Appl. No.: 15/754,983

(22) PCT Filed: Aug. 26, 2016

(86) PCT No.: PCT/AU2016/050799
§ 371 (c)(1),
(2) Date: Feb. 23, 2018

(87) PCT Pub. No.: WO2017/031551
PCT Pub. Date: Mar. 2, 2017

(65) Prior Publication Data
US 2020/0232038 A1  Jul. 23, 2020

(30) Foreign Application Priority Data

Aug. 26, 2015  (AU) ................................ 2015903456

(51) Int. Cl.
*C12Q 1/6886* (2018.01)
*C12Q 1/34* (2006.01)

(52) U.S. Cl.
CPC ............. *C12Q 1/6886* (2013.01); *C12Q 1/34* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

| WO | WO-1997022596 | 6/1997 |
|----|---------------|--------|
| WO | WO-1997030035 | 8/1997 |
| WO | WO-1997032856 | 9/1997 |
| WO | WO-1998013354 | 4/1998 |
| WO | WO-1999002166 | 1/1999 |
| WO | WO-2000040529 | 7/2000 |
| WO | WO-2000041669 | 7/2000 |
| WO | WO-2001092224 | 12/2001 |
| WO | WO-2002004434 | 1/2002 |
| WO | WO-2002008213 | 1/2002 |
| WO | WO-2014066955 | 5/2014 |
| WO | WO-2017031551 | 3/2017 |

OTHER PUBLICATIONS

Bass, Brenda L., "RNA Editing by Adenosine Deaminases That Act on RNA", Annual Review of Biochemistry, vol. 71, (2002), 817-846.
Beale, R. C., "Comparison of the differential context-dependence of DNA deamination by APOBEC enzymes: correlation with mutation spectra in vivo", Journal of Molecular Biology, 337(3), (Apr. 2004), 12 pgs.
Burns, Michael B., "APOBEC3B is an enzymatic source of mutation in breast cancer", Nature, 494 (7437), (Feb. 2013), 13 pgs.
Farajollahi, S., "2010 Molecular diversity through RNA editing: a balancing act", Trends Genet, 26(5), (May 2010), 18 pgs.
Honjo, T., "The AID dilemma: infection, or cancer?", Advances in Cancer Research, vol. 113, (2012), 44 pgs.
Kanchi, Krishna L., "Integrated analysis of germline and somatic variants in ovarian cancer", Nature Communications, 5(3156), (2014), 29 pgs.
Leonard, Brandon, "APOBEC3B Upregulation and Genomic Mutation Patterns in Serous Ovarian Carcinoma", Cancer Research, 73(24), (Oct. 2013), 26 pgs.
Maul, Robert W., "AID and somatic hypermutation", Adv Immunol, 105, (2010), 27 pgs.
Nabel, Christopher S., "AID APOBEC deaminases disfavor modified cytosines implicated in DNA demethylation". Nature Chemical Biology, 8(9), (Sep. 2012), 17 pgs.
Steele, Edward J., "Somatic mutation patterns in non-lymphoid cancers resemble the strand biased somatic hypermutation spectra of antibody genes", DNA Repair, 9(6), (2010), 17 pgs.
Nik-Zainal, Serena, et al., "Mutational Processes Molding the Genomes of 21 Breast Cancers", Cell 149, (2012), 979-993.
Steele, Edward J., "Somatic hypermutation in immunity and cancer: Critical analysis of strand-biased and codon-context mutation signatures", DNA Repair, vol. 45, (Sep. 2016), 1-24.
Lindley, Robyn A., et al., "Association between targeted somatic mutation (TSM) signatures and HGS-OvCa progression", Cancer Medicine 2016; 5(9):2629-2640, (Jun. 13, 2016), 2629-2640.
Lindley, Robyn A., "The importance of codon context for understanding the Ig-like somatic hypermutation strand-biased patterns in TP53 mutations in breast cancer", Cancer Genetics, vol. 206, Issue 6 (2013), (May 10, 2013), 222-226.
"International Application No. PCT AU2016 050799, International Search Report and Written Opinion dated Oct. 26, 2016", (Oct. 26, 2016), 15 pgs.
"European Application Serial No. 16838136.6, Extended European Search Report dated Feb. 25, 2019", 12 pgs.

*Primary Examiner* — Joseph Woitach
(74) *Attorney, Agent, or Firm* — Schwegman Lundberg & Woessner, P.A.

(57) ABSTRACT

Disclosed are methods of detecting the likelihood of cancer recurrence. More particularly, the present invention discloses methods of identifying nucleic acid signatures that correlate with the likelihood of cancer recurrence, and methods of using such signatures.

3 Claims, 3 Drawing Sheets

METHODS OF DETECTING CANCER RECURRENCE

PRIORITY CLAIM TO RELATED APPLICATIONS

This application is a U.S. national stage filing under 35 U.S.C. § 371 from International Application No. PCT/AU2016/050799, filed on 26 Aug. 2016, and published as WO2017/031551 on 2 Mar. 2017, which claims the benefit under 35 U.S.C. 119 to Australia Application No. 2015903456, filed on 26 Aug. 2015; the benefit of priority of each of which is claimed herein, and which applications and publication are hereby incorporated herein by reference in their entirety.

FIELD OF THE INVENTION

This invention relates generally to methods of detecting the likelihood of cancer recurrence. More particularly, the present invention relates to methods of identifying nucleic acid signatures that correlate with the likelihood of cancer recurrence, and methods of using such signatures.

BACKGROUND OF THE INVENTION

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

The human genome has evolved to encode many enzymes capable of deaminating either single stranded DNA (ssDNA) or double stranded (dsRNA) conformations during transcription. These deaminase enzymes constitute a powerful antiviral response, as few viruses can survive such a high rate of mutation. However, when regulation of DNA and RNA deaminase activity breaks down, these enzymes attack nucleic acids in normal somatic tissue during transcription. The result is an accumulation of unwanted de novo mutations that may ultimately give rise to diseases, for example, cancer (see, Paz et al., 2007; Honjo et al., 2008; Steele and Lindley, 2010; and Lindley and Steele, 2013).

There are two different families of deaminases: the cytidine deaminases, and the adenosine deaminases. The cytidine deaminase family of enzymes constitutes a set of differentially expressed enzymes capable of deaminating cytosine (in effect, substituting cytosine for uracil) in ssDNA. The most widely studied cytidine deaminase is activation induced deaminase (AID). While AID is primarily expressed in activated B-cells undergoing immunoglobulin (Ig) somatic hypermutation (SHM) and Ig class switch recombination, AID activity has long been identified in most somatic tissues. It is involved in the early mutagenic events leading to cancers in non-lymphoid cells (see, Okazaki et al, 2003), and it has been shown to target both the transcribed strand (TS) and the non-transcribed strand (NTS) of ssDNA in the nucleus during transcription (see, Maul and Gearheart, 2010; Basu et al., 2011; and Lindley 2013). It has also been experimentally demonstrated that the estrogen receptor complex binds to the AID promotor region (see, Pauklin 2009), triggering an increase in AID messenger RNA expression, and leading to a greater than 20-fold increase in AID production in breast and ovarian tissue. Estrogen antagonists such as the widely prescribed Tamoxifen, are therefore effective at inhibiting AID production in somatic tissue.

The apolioprotein B mRNA-editing enzyme-catalytic polypeptide-like cytidine deaminases (APOBECs) form a family of 11 or more orthologous cytidine deaminases. This family of enzymes are known to contribute to the development of many cancers (see, Roberts, 2013), and most are tissue specific (see, Conticello 2008, Table 2). For example, APOBEC1 is found in high concentrations in the small intestine, APOBEC2 is found at significant levels in skeletal and heart muscles, APOBEC4 is found in testis, and APOBEC3H is found in the blood, thymus, and thyroid.

The human APOBEC3 deaminases have a range of functions that include providing innate immunity to a range of DNA-based parasites, including retroviruses and DNA viruses and naked DNA with susceptible cDNA intermediates during transcription. They are related to, and may even be an evolutionary precursor of AID, and the APOB mRNA editing enzyme APOBEC1.

The most studied APOBEC3 deaminases are APOBEC3G and APOBEC3B. Both of these enzymes are expressed at significant levels in many if not all somatic tissues. APOBEC3G is an evolutionarily conserved cytidine deaminase that potently restricts retrotransposons and other viruses. It was first identified as the main factor involved in HIV restriction (see, Sheehy, 2002). Several studies suggest that APOBEC3B-catalyzed deamination is responsible for a large proportion of mutations in a range of cancers (see, Leonard et al, 2013; and Sasaki, 2014), and that this process provides a chronic source of DNA damage in ovarian cancers (see, Burns et al, 2013a) and breast cancer (see, Burns 2013b).

The adenosine deaminases bind to completely or partially double stranded RNA (dsRNA) and convert adenosine to inosine (in effect, substituting A for I). Inosine codes as guanosine during translation (see, Bass 2002). The ADAR1, ADAR2 and ADAR3 genes have been identified in humans. While it is well established that there are different splice variants for each ADAR, it is unknown if or how each splice variant may exhibit different deaminase binding domains (DBDs) for targeting (see, Farajollahi and Maas, 2010). A number of variant ADAR species with polymorphisms are expressed in a range of somatic tissues (see, George et al, 2005).

Two immunologically related forms of ADAR1 have been shown to exist in many somatic tissues, (see, George and Samuel, 1999). ADAR2 is found in many tissues with especially large concentrations in the human brain. Most ADAR proteins are localized in the nucleus, except for ADAR1 which is shuttled between the nucleus and the cytoplasm. Although the adenosine deaminases have been suggested to play a role in tumourigenesis, the mechanism by which they do so is yet to be established.

Editing by ADARs drives the generation of RNA and protein diversification in eukaryotes, and their RNA-editing role is more important in higher organisms. Their role includes recoding exons via reverse transcription of the edited site(s) in RNA, editing of retrotransposon-derived repeat elements and mRNA sequence modification (see, Farajollahi and Maas, 2010). Given the diverse range of impacts that ADAR-editing has on gene expression, dysregulation of ADAR1 and ADAR2 conformation and expression are linked to cancer phenotypes. A general decrease in RNA editing activity has been associated with disease progression (see, Gallo and Galardi, 2008), ADAR1 has been identified as a tumour promotor, and ADAR2 as a tumour suppressor (see, Chan et al, 2014). The diversity generated by aberrant A-to-I editing of the protein-coding exons in pre-mRNAs therefore significantly alters gene expression in human cancers.

It is now widely agreed that aberrant cytidine and adenosine deaminase activity are heavily implicated in oncogenic processes. However, no specific biomarkers suitable for detecting cancer have yet been elucidated. Previous work has enabled us to begin to understand that the targeting preferences of the deaminases is far more specific than previously thought. A study of TP53 mutations occurring in pooled breast cancer mutation data established that the molecular mechanisms involved in generating targeted somatic mutations relies upon the ability to sense codon reading frame structure at the level of ssDNA during transcription, as well as the ability to differentiate between cytosines on the non-transcribed strand (NTS) and those on the transcribed strand (TS) (see, Lindley 2013).

Around 24,000 women are diagnosed with ovarian cancer each year in the United States alone, with the average five-year survival being only around 44% (see, Howlader et al, 2013). Most ovarian cancer patients are treated with aggressive surgery followed by platinum-taxane chemotherapy. Of those that undergo treatment, platinum-resistance cancer recurs in around 25% of patients within six months. (see, Miller, 2009). As most deaths are the result of late-stage diagnosis, understanding the contributing genetic factors is an important step for the development of new screening strategies.

Particularly needed in the art is a means of identifying biomarkers for ovarian and other cancers that can be used in a genetic assay to predict recurrence or progression of disease following intervention (i.e., by surgical, radiological, pharmaceutical or other means).

SUMMARY OF THE INVENTION

The present invention is predicated in part on the determination that the targeted somatic mutation (TSM) phenomena make it possible to identify individual deaminase-binding domains (DBD) as the source of many somatic mutations that arise during oncogenesis. This identification led to the discovery that new DBDs are developed as disease progresses. Accordingly, the methods disclosed herein are used to identify nucleotide motifs defining isoforms of DBD that are associated with disease progression indicators (referred to as "Cancer-Progression Associated Signatures" (C-PAS)). In one aspect, the present invention provides a novel genetic assay using one or more C-PAS to predict the probability of recurrence (or progression) of a cancer in a subject.

In its broadest form, the present invention provides a method for determining the likelihood that a cancer will recur in a subject, the method comprising: (a) analysing the sequence of a nucleic acid molecule in a biological sample obtained from the subject to determine for a plurality of mutations of a mutation type at one or more motifs recognized or targeted by a mutagenic agent the codon context of those mutations to thereby identify the location of a mutation and mutation type for each of a plurality of mutated codons in the nucleic acid molecule, wherein the codon context of an individual mutation is determined by determining at which of the three positions of a corresponding mutated codon the individual mutation occurs; and (b) determining the likelihood of cancer recurrence in the subject when a level of mutation of a mutation type at one of the three positions in the plurality of mutated codons is above a predetermined threshold that correlates with the recurrence of the cancer.

One advantage of this method is that it allows for a treatment regimen for a subject who has or has had a cancer, to be prescribed based on the determination of the likelihood that the cancer will recur. For example, if a cancer is determined as being likely to recur in a subject, the subject may continue a heavy course of anti-cancer therapy. Conversely, if a cancer is determined to be unlikely to recur in a subject, the subject may discontinue, reduce, or change an existing anti-cancer therapy.

In some embodiments of this type, the nucleic acid molecule is present in a biological sample obtained from the subject. Preferably, the biological sample is obtained from the tissue that is, or was previously, affected with the cancer in the subject. By using a biological sample obtained from the tissue affected with cancer, or known to have an increased risk of developing cancer, tissue-specific DBD can be identified to create a diagnostic/prognostic test with higher specificity and sensitivity.

In some embodiments, the mutagenic agent that causes the TSM is selected from the group comprising, consisting or consisting essentially of: AID, APOBECs, and ADARs. In some embodiments, targeted somatic mutagenesis caused by a single mutagenic agent is assessed. In other embodiments, targeted somatic mutagenesis caused by 2, 3, 4, 5, 6, 7, 8, 9, 10, or more than 10 mutagenic agents is assessed.

By way of an illustrative example, when the sample is an ovarian tissue sample and the mutagenic agent is an oncogenic isoform of AID, a determination that cancer recurrence is likely will be made when the level of C to T mutations in WRCGSS motifs at MC-1 sites of a nucleic acid molecule present in a biological sample is above a predetermined threshold.

In another example, when the sample is an ovarian tissue sample and the mutagenic agent is an APOBEC3B, a determination that cancer recurrence is likely is made when the level of C to T mutations in TCGA motifs at MC-1 sites or MC-3 sites of a nucleic acid molecule present in a biological sample is above a predetermined threshold; or when the level of C to T mutations in ATCS motifs at MC-3 sites of a nucleic acid molecule present in a biological sample is above a predetermined threshold.

In yet another example, when the sample is an ovarian tissue sample and the mutagenic agent is APOBEC3G, a determination that cancer recurrence is likely is made when the level of C to T mutations in GCGGC motifs at MC-1 sites of a nucleic acid molecule present in a biological sample is above a predetermined threshold; the level of C to T mutations in CCGX motifs at MC-1 sites of a nucleic acid molecule present in a biological sample is above a predetermined threshold; when the level of C to T mutations in ZCCS motifs at MC-1 sites of a nucleic acid molecule present in a biological sample is above a predetermined threshold; when the level of G to A mutations in SGGRR motifs at MC-1 sites of a nucleic acid molecule present in a biological sample is above a predetermined threshold; when the level of C to T mutations in TCCG motifs at MC-1 sites of a nucleic acid molecule present in a biological sample is above a predetermined threshold; when the level of G to A mutations in GCGC motifs at MC-2 sites of a nucleic acid molecule present in a biological sample is above a predetermined threshold; or when the level of G to A mutations in CCGGC motifs (i.e., C-PAS) at MC-2 sites of a nucleic acid molecule present in a biological sample is above a predetermined threshold.

In yet another example, when the sample is an ovarian tissue sample and the mutagenic agent is an oncogenic ADAR isoform, such as ADAR1, a determination that cancer recurrence is likely when the level of A to T mutations in RAW<u>A</u> motifs at MC-1 sites of a nucleic acid molecule present in a biological sample is above a predetermined threshold; when the level of A to G mutations in WT<u>A</u>W motifs at MC-1 sites of a nucleic acid molecule present in a biological sample is above a predetermined threshold; when the level of A to G mutations in SAR<u>A</u> motifs at MC-1 sites of a nucleic acid molecule present in a biological sample is above a predetermined threshold; or when the level of T to C mutations in <u>T</u>WTY motifs at MC-2 sites or MC-3 sites of a nucleic acid molecule present in a biological sample is above a predetermined threshold.

In another illustrative example of the invention, the subject has, or is at risk of developing, acute myeloid leukeamia (AML). For example, when the sample is a blood sample and the mutagenic agent is an oncogenic APOBEC isoform, a determination that cancer recurrence is likely will be made when the level of C to T mutations in C<u>C</u>Z motifs at MC-1 sites of a nucleic acid molecule from a biological sample is above a predetermined threshold; or when the level of C to T mutations in SW<u>C</u>S motifs at MC-2 sites of a nucleic acid molecule from a biological sample is above a predetermined threshold; or when the G to A mutations in XN<u>G</u>NS motifs at MC-3 sites of a nucleic acid molecule from a biological sample is above a predetermined threshold; or when the level of G to A mutations in <u>G</u>SA motifs at MC-2 sites of a nucleic acid molecule from a biological sample is above a predetermined threshold; or when the level of G to A mutations in S<u>G</u>XW motifs at MC-1 sites of a nucleic acid molecule from a biological sample is above a predetermined threshold; or when the level of G to A mutations in CX<u>GS</u> motifs at MC-3 sites of a nucleic acid molecule from a biological sample is above a predetermined threshold; or when the level of G to A mutations in YX<u>G</u>NX motifs at MC-3 sites of a nucleic acid molecule from a biological sample above a predetermined threshold; or when the level of G to A mutations in YY<u>G</u>NX motifs at MC-3 sites of a nucleic acid molecule from a biological sample is above a predetermined threshold; or when the level of G to A mutations in WN<u>G</u>NZ motifs at MC-1 sites of a nucleic acid molecule from a biological sample is above a predetermined threshold.

In preferred embodiments, the nucleic acid molecule is characterized for the level of targeted somatic mutations in a plurality of defined motifs targeted by one or more mutagenic agents. For example, in some embodiments targeted somatic mutations in 2, 3, 4, 5, 6, 7, 8, 9, 10, or more than 10, motifs are determined.

In some embodiments a cancer is assessed as being likely to recur if the level of TSM (i.e., as identified in C-PAS) is above a predetermined threshold. The predetermined threshold can be defined by any method suitable for distinguishing between subject groups. In this regard, the predetermined threshold could be a fixed number of targeted somatic mutations per sample that is set at an appropriate value for distinguishing between cancers that are likely to recur and cancers that are not likely to recur. For example, as clearly shown in Example 4 (see, for example Table 7), subjects known to have successfully overcome ovarian cancer without recurrence are demonstrated to have a maximum of one C-PAS in a sample attributed to any single mutagenic agent. Thus, by way of a non-limiting example, the predetermined threshold for determining an increased likelihood of ovarian cancer recurrence could be one C-PAS. In this example, any subject with more than one C-PAS in the nucleic acid molecule would be considered to have a high likelihood of cancer recurrence. Similarly, an individual with less than one C-PAS in a nucleic acid molecule would be determined not likely to have cancer recurrence.

Alternatively, when the predetermined threshold is referring to the frequency of sample mutations being indicative of TSM, the predetermined threshold could be the frequency of mutations that would be expected if a particular mutation occurred randomly. Thus, if a higher than expected frequency of mutation is observed in a nucleic acid molecule present in a biological sample, a determination can made that TSM has occurred, C-PAS may be identified, and that the cancer is likely to recur.

In some embodiments, the method is suitable for determining the likelihood of recurrence of any cancer. For example, the cancer can be selected from among ovarian, breast, prostate, liver, colon, stomach, pancreatic, skin, thyroid, cervical, lymphoid, hematopoietic, bladder, lung, renal, rectal, uterine, and head and neck cancer. Typically, the biological sample is prepared from tissue in which the cancer is present. For example, if a subject has or is at risk of developing ovarian cancer, a biological sample is prepared from ovarian cells or tissue. Similarly, if a subject has or is at risk of developing breast cancer, a biological sample is prepared from breast cells or tissue. Other biological samples suitable for performing the methods of the present invention include, but are not limited to, prostate, liver, colon, stomach, pancreatic, skin, thyroid, cervical, lymphoid, hematopoietic, bladder, lung, renal, rectal, uterine, and head or neck tissue or cells.

In another aspect, the present invention provides methods of identifying Cancer-Progression Associated Signatures ("C-PAS") that are indicative of the likelihood of cancer recurrence in a subject, the method comprising: analysing for a first subject group, nucleic acid sequences to determine for a plurality of mutations of a mutation type at one or more motifs recognized or targeted by a mutagenic agent the codon context of those mutations to thereby identify the location of a mutation and mutation type for each of a plurality of mutated codons in the nucleic acid sequences, wherein the codon context of an individual mutation is determined by determining at which of the three positions of a corresponding mutated codon the individual mutation occurs, wherein the first subject group consists of subjects who have had recurrence of the cancer; determining that targeted somatic mutagenesis (TSM) has occurred when a level of mutation of a mutation type at one of the three positions in the plurality of mutated codons is above that which would be expected to occur if the mutation occurred randomly and independently of codon context; and identifying the TSM as being part of a C-PAS when the TSM, or a nucleic acid sequence comprising the TSM, is capable of distinguishing between a second subject group and a third subject group, wherein the second subject group consists of subjects who have the cancer, or those in which the cancer is known to recur, and the third subject group consists of subjects in which the cancer is known not to recur.

In yet another aspect, the present invention provides a method of treating a cancer or inhibiting recurrence a cancer in a subject, the a method comprising: (i) identifying C-PAS by the methods described above and elsewhere herein for the tissue in which the cancer is present in the subject; (ii) obtaining a biological sample from the subject, wherein the biological sample contains tissue of cells having the cancer, or at risk of developing the cancer; (iii) analyzing a nucleic acid molecule in the biological sample for the presence or absence of C-PAS, to determine whether the cancer or tumour is likely to recur; and (iv) exposing the subject to a therapy on the basis that the cancer is determined as likely to recur in the subject.

In yet still another aspect, the present invention provides methods of administering a treatment regimen or therapy for a subject with a cancer, or a subject in which a cancer is likely to recur. In some embodiments, the methods comprise determining whether a cancer is likely to recur according to the identification and determination methods described above and elsewhere herein, and exposing the subject to a treatment regimen that is best suited for the subject on the basis of the likelihood of the cancer recurring. Suitable treatment regimens for treating a cancer are well known in the art, and described in detail below. In some embodiments, the therapy or treatment regimen comprises radiotherapy, surgery, chemotherapy, hormone ablation therapy, pro-apoptosis therapy and/or immunotherapy.

When recurrence of a cancer is determined to be likely in a subject, the subject will be prescribed and exposed to an appropriate treatment regimen. An advantage of the methods of the present invention is that once the TSM in a nucleic acid molecule in a biological sample has been determined, a personalised treatment regimen can be prescribed in light of the subject's individual TSM profile. For example, if TSM is identified as being caused by an aberration or dysregulation of AID in the biological sample, chemotherapy can be in the form of an AID inhibitor, an APOBEC3G inhibitor. In other examples, an APOBEC1 inhibitor or an APOBEC3H inhibitor, an ADAR inhibitor may be more suitable depending on the individual TSM that is observed in the biological sample obtained from the subject.

When recurrence of a cancer is determined to be unlikely in a subject, the existing treatment regimen that the subject may have been exposed to could be discontinued, reduced or changed. The treatment regimens currently standard in the art for treating cancer (e.g., ovarian cancer or AML) have many undesirable side effects. Accordingly, discontinuing and/or reducing the treatment regimen exposed to a subject on the determination that a cancer is unlikely to recur is beneficial.

BRIEF DESCRIPTION OF THE FIGURES

An example of the present invention will now be described with reference to the accompanying drawings, in which: —

DETAILED DESCRIPTION OF THE INVENTION

1. Definitions

Figure 1:
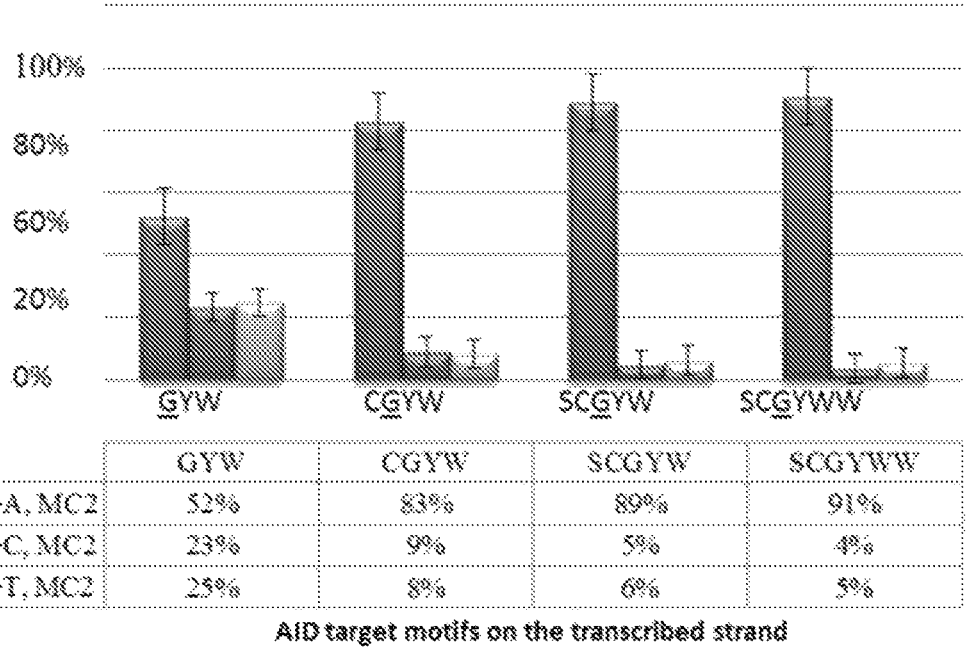
FIG. 1 shows a graph showing how the targeting specificity for G to A mutations is increased as the number of nucleotides defining the target motif is incrementally increased from three nucleotides to six nucleotides. A plot of the number of G to A mutations compared to G to C and G to T off the second nucleotide sites within the mutated codon (MC-2, read 5-prime (5') to 3-prime (3')), and starting with the well-known GYW motif associated with AID deamination activity. For the motifs, W=A/T; S=C/G; and Y=T/C. All of the selected motifs show a preference for targeting the second position within the mutated codon (i.e., MC-2 sites), and the dominant resulting mutation is a G to A. The percentage of each type of mutation off G at MC-2 sites is shown. A targeted somatic mutation (TSM) 3×3 table for each motif, and showing all possible mutations and target sites within the mutated codon is included. MC-1, MC-2, and MC-3 refer to the position of the mutations within the mutated codon (MC), read 5-prime (5') to 3-prime (3'). The Chi square level of statistical significance (<0.001, 8 df) for deviation from the expected distribution of mutations by type and location within the mutated codon for each motif is shown in the column on the far right.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "a glycospecies biomarker" means one glycospecies biomarker or more than one glycospecies biomarker.

As used herein, "and/or" refers to and encompasses any and all possible combinations of one or more of the associated listed items, as well as the lack of combinations when interpreted in the alternative (or).

The term "about", as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

The term "biological sample" as used herein refers to a sample that may be extracted, untreated, treated, diluted or concentrated from a subject or patient. Suitably, the biological sample is selected from any part of a patient's body, including, but not limited to hair, skin, nails, tissues or bodily fluids such as saliva and blood.

As used herein, the term "codon context" with reference to a mutation refers to the nucleotide position within a codon at which the mutation occurs. For the purposes of the present invention, the nucleotide positions within a mutated codon (MC; i.e., a codon containing the mutation) are annotated MC-1, MC-2 and MC-3, and refer to the first, second and third nucleotide positions, respectively, when the sequence of the codon is read 5' to 3'. Accordingly, the phrase "determining the codon context of a mutation" or similar phrase means determining at which nucleotide position within the mutated codon the mutation occurs, i.e., MC-1, MC-2 or MC-3.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements.

The term "control subject", as used in the context of the present invention, may refer to a subject known to be affected with a cancer (positive control), or to a subject known to be not affected or diagnosed with a cancer condition (negative control). It should be noted that a control subject that is known to be healthy, i.e., not suffering from a cancer, may possibly suffer from another disease not tested/known. It is also understood that control subjects and healthy controls include data obtained and used as a standard, i.e., it can be used over and over again for multiple different subjects. In other words, for example, when comparing a subject sample to a control sample, the data from the control sample could have been obtained in a different set of experiments, for example, it could be an average obtained from a number of healthy subjects and not actually obtained at the time the data for the subject was obtained.

The term "correlating" generally refers to determining a relationship between one type of data with another or with a state. In various embodiments, correlating TSM with the presence or absence of a cancer comprises determining the level of TSM in a subject that suffers from a cancer, or in persons known to be free of cancer. In specific embodiments, the level of TSM is correlated to the recurrence of cancer using receiver operating characteristic (ROC) curves.

By "gene" is meant a unit of inheritance that occupies a specific locus on a genome and comprises transcriptional and/or translational regulatory sequences and/or a coding region and/or non-translated sequences (i.e., introns, 5' and 3' untranslated sequences).

As used herein, the term "likelihood" is used as a measure of whether TSM has occurred, and of whether subjects with nucleic acid molecule containing targeted somatic mutations will experience a recurrence of a cancer based on a given mathematical model. An increased likelihood for example may be relative or absolute and may be expressed qualitatively or quantitatively. For instance, an increased likelihood or risk that a subject will develop cancer may be expressed as simply determining the number of targeted somatic mutations (as taught herein) and placing the test subject in an "increased likelihood or risk" category, based upon previous population studies.

In some embodiments, the methods comprise comparing the number or percentage of targeted somatic mutations to a preselected or threshold number or percentage. Thresholds may be selected that provide an acceptable ability to predict diagnosis, likelihood or prognostic risk. In illustrative examples, receiver operating characteristic (ROC) curves are calculated by plotting the value of a variable versus its relative frequency in two populations in which a first population has a first condition or risk and a second population has a second condition or risk (called arbitrarily, for example, "healthy condition" and "cancer", or "low risk" and "high risk").

A distribution of number of mutations for subjects who experience recurrence and who do not experience recurrence will likely overlap. Under such conditions, a test does not absolutely distinguish between a recurring cancer and a cancer that will not recur with 100% accuracy. A threshold is selected, above which the test is considered to be "positive" and below which the test is considered to be "negative." The area under the ROC curve (AUC) provides the C-statistic, which is a measure of the probability that the perceived measurement will allow correct identification of a condition (see, for example, Hanley et al, *Radiology* 143: 29-36 (1982)). The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., a healthy condition mutation status and a cancer mutation status). ROC curves are useful for plotting the performance of a particular feature in distinguishing or discriminating between two populations (e.g., cases having a cancer and controls without the cancer). Typically, the feature data across the entire population (e.g., the cases and controls) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to produce a single value, and this single value can be plotted in a ROC curve. Additionally, any combination of multiple features (e.g., one or more other epigenetic markers), in which the combination derives a single output value, can be plotted in a ROC curve. These combinations of features may comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one. An AUC ROC value may be thought of as equivalent to the Mann-Whitney U test, which tests for the median difference between scores obtained in the two groups considered if the groups are of continuous data, or to the Wilcoxon test of ranks.

Alternatively, or in addition, thresholds may be established by obtaining an earlier mutation status result from the same patient, to which later results may be compared. In these embodiments, the individual in effect acts as their own "control group." In another embodiment, thresholds may be established by analyzing the number targeted somatic mutations in nucleic acid molecules from non-diseased or healthy tissue from a patient and comparing it to analyzing the number targeted somatic mutations in nucleic acid molecules from diseased or cancerous tissue.

The term "diagnosis" as used in the context of the present invention refers to the process of determining the likelihood of cancer recurrence. The determination of TSM in a nucleic acid molecule present in a biological sample from a subject correlates with likelihood of cancer recurrence in a subject.

As used herein, a "healthy" subject is a subject that does not have cancer and is not likely to have recurrence of cancer.

As used herein, "level" with reference to a TSM refers to the number, percentage or amount of TSM in a nucleic acid molecule that is present in a biological sample. The number, percentage or amount TSM may be absolute or may be relative, and can be determined using any method known in the art.

The term "mutagenic agent" refers to an endogenous (i.e., agents that are endogenous to, or are produced by, the cell in which the DNA is contained) agent that can cause mutagenesis of DNA or RNA.

As used herein, a "mutation type" refers to the specific nucleotide substitution that comprises the mutation, and is selected from among C to T, C to A, C to G, G to T, G to A, G to C, A to T, A to C, A to G, T to A, T to C and T to G mutations. Thus, for example, a mutation type of C to T refers to a mutation in which the targeted or mutated nucleotide C is replaced with the substituting nucleotide T.

The "nucleic acid" as used herein designates DNA, cDNA, mRNA, RNA, rRNA or cRNA. The term typically refers to polynucleotides greater than 30 nucleotide residues in length.

As used herein, the terms "recur," "recurrence" and the like refer to the re-growth of tumour or cancerous cells in a subject after a primary treatment for the cancer or tumour has been administered. The tumour may recur in the original site or in another part of the body. In one embodiment, a tumour that recurs is of the same type as the original tumour for which the subject was treated. For example, if a subject had an ovarian cancer tumour, was treated for and subsequently developed another ovarian cancer tumour, the tumour has recurred. In addition, a cancer can recur in or metastasize to a different organ or tissue than the organ or tissue where it originally occurred.

The term "sensitivity", as used herein, refers to the probability that a diagnostic or predictive method or kit of the present invention gives a positive result when the biological sample is positive, e.g., having the predicted diagnosis. Sensitivity is calculated as the number of true positive results divided by the sum of the true positives and false negatives. Sensitivity essentially is a measure of how well the present invention correctly identifies those who have the predicted diagnosis from those who do not have the predicted diagnosis. The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "somatic mutation" refers to a mutation in the DNA of somatic cells (i.e., not germ cells), occurring after conception. "Somatic mutagenesis" therefore refers to the process by which somatic mutations occur.

The term "specificity", as used herein, refers to the probability that a diagnostic or predictive method or kit of the present invention gives a negative result when the biological sample is not positive, e.g., not having the predicted diagnosis. Specificity is calculated as the number of true negative results divided by the sum of the true negatives and false positives. Specificity essentially is a measure of how well the present invention excludes those who do not have the predicted diagnosis from those who do have the predicted diagnosis. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The terms "subject", "individual" or "patient", used interchangeably herein, refer to any animal subject, particularly a mammalian subject. By way of an illustrative example, suitable subjects are humans. In some embodiments, the subject presents with clinical signs of a condition as defined herein. As used herein, the term "clinical sign", or simply "sign", refers to objective evidence of a disease present in a subject. Symptoms and/or signs associated with diseases referred to herein and the evaluation of such signs are routine and known in the art. Examples of signs of disease vary depending upon the disease. Signs of a cancer may include tumourigenesis, metastasis, and angiogenesis. Typically, whether a subject has a disease, and whether a subject is responding to treatment, may be determined by evaluation of signs associated with the disease.

As used herein, the terms "targeted somatic mutagenesis" and "TSM" refer to the process of somatic mutagenesis resulting from one or more mutagenic agents, wherein mutagenesis occurs at a targeted nucleotide within a motif, the targeted nucleotide is present at a particular position within a codon (e.g., the first, second or third position of the mutated codon reading from 5' to 3', annotated MC-1, MC-2 and MC-3, respectively), and the targeted nucleotide is mutated to a particular substituting nucleotide (i.e., the mutation is of a particular mutation type, e.g., C to T, not C to A or C to G). Thus, a determination that TSM is occurring requires analysis of the type of mutation (e.g., C to T), the motif at which the mutation occurs (e.g., WR<u>C</u>) and codon context of the mutation, i.e., the position within the codon at which the mutation occurs (e.g., MC-1, MC-2 or MC-3). "Targeted somatic mutagen" therefore refers to mutation resulting from TSM.

The terms "treat" and "treating" as used herein, unless otherwise indicated, refer to both therapeutic treatment and prophylactic or preventative measures, wherein the object is to inhibit, either partially or completely, ameliorate or slow down (lessen) recurrence of the targeted condition or disorder (e.g., a cancer), or one or more symptom associated therewith. The terms are also used herein to denote delaying the onset of, inhibiting (e.g., reducing or arresting the growth of), alleviating the effects of, or prolonging the life of a patient suffering from, cancer, in particular, a cancer or tumour. Those in need of treatment include those diagnosed with the disorder, those suspected of having the disorder, those predisposed to have the disorder as well as those in whom the disorder is to be prevented. Hence, the subject to be treated herein may have been diagnosed as having the disorder or may be predisposed or susceptible to the disorder. In some embodiments, treatment refers to the eradication, removal, modification, or control of primary, regional, or metastatic cancer tissue that results from the administration of one or more therapeutic agents according to the methods of the invention. In other embodiments, such terms refer to the minimizing or delaying the spread of cancer resulting from the administration of one or more therapeutic agents to a subject with such a disease. In other embodiments, such terms refer to elimination of disease causing cells. The term "treatment" as used herein, unless otherwise indicated, refers to the act of treating.

As used herein, the term "treatment regimen" refers to prophylactic and/or prophylactic regimen (i.e., before the onset of a cancer or tumour), or to a therapeutic regimen (i.e., after the onset of a cancer). The term "treatment regimen" encompasses natural substances and pharmaceutical agents (i.e., "drugs") as well as any other treatment regimen including but not limited to chemotherapy, radiotherapy, proton therapy, immunotherapy, hormone therapy, phototherapy, cryotherapy, cryosurgery, toxin therapy or pro-apoptosis therapy, high intensity focused ultrasound, dietary treatments, physical therapy or exercise regimens, surgical interventions, and combinations thereof.

Those skilled in the art will appreciate that the aspects and embodiments described herein are susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features.

2. Abbreviations

The following abbreviations are used throughout the application:
ADAR=adenosine deaminases acting on RNA
AID=activation-induced cytidine deaminase
APOBEC=apolipoprotein B mRNA-editing enzyme, catalytic polypeptide-like (APOBEC) cytidine deaminases
DBD=deaminase-binding domain
NTS=non-translated strand
SHM=somatic hypermutation
TSM=Targeted somatic mutation
nt=nucleotide
nts=nucleotides
aa=amino acid(s)
kb=kilobase(s) or kilobase pair(s)
kDa=kilodalton(s)
ds=double stranded
ss=single stranded
d=day
h=hour
s=seconds

TABLE 2

IUPAC Nucleotide Symbols

| SYMBOL | DESCRIPTION |
|---|---|
| A | Adenosine |
| C | Cytidine |
| G | Guanosine |
| T | Thymidine |
| U | Uridine |
| M | Amino (adenosine or cytosine) |
| K | Keto (guanosine or thymidine) |
| R | Purine (adenosine or guanosine) |
| Y | Pyrimidine (cytosine or thymidine) |
| S | Strong (guanosine or cytosine) |
| W | Weak (adenosine or thymine) |
| B | Cytosine, guanosine, or thymine |
| D | Adenosine, guanosine or thymidine |
| H | Adenosine, cytosine or thymidine |
| V | Adenosine, cytosine or guanosine |
| N | Any nucleotide |

3. Mutagenic Agents Involved in Somatic Mutagenesis

The present invention is predicated in part on the unexpected finding that one or more specific mutations associated with TSM correlates with the likelihood that a cancer will recur in a subject. The present invention encompasses methods for identifying such mutations as well as methods for determining the likelihood that a cancer will recur in a subject by detecting those mutations Endogenous factors (e.g., enzymes) can act as mutagenic agents that cause or play a role in somatic mutagenesis. Endogenous factors include, but are not limited to, cytidine deaminases (such as activation-induced cytidine deaminase (AID) and apolipoprotein B mRNA-editing enzyme and catalytic polypeptide-like (APOBEC) cytidine deaminases), adenosine deaminases such as adenosine deaminases acting on RNA, and error-prone DNA polymerases such as DNA polymerase eta. Notably, many of these deaminases have specific isoforms that are present in each tissue type.

3.1 Activation-Induced Cytidine Deaminase (AID)

Activation-induced cytidine deaminase (AID) is an important enzyme in adaptive immunity, involved in somatic hypermutation (SHM) and class switch recombination of immunoglobulin genes in B cells. AID triggers SHM by deaminating cytidines to uracils (C to U) to diversify the immunoglobulin variable region genes (VDJ) and create new antigen-binding sites. By convention, mutations of C (e.g., C to T) are the result of cytosine deamination that occurs on the non-transcribed strand (NTS). Conversely, mutations of G (e.g., G to A) are the result of cytosine deamination that occurs on the transcribed strand (TS).

In some embodiments of the present invention, wherein the cancer is an ovarian cancer (e.g., serous ovarian adenocarcinoma) and the biological sample comprises ovarian cells and/or tissue, AID targets a motif comprising the nucleic acid sequence WRCG/CGYW (where W=A/T; R=A/G; and Y=T/C). Specifically, TSM is likely to have occurred if a higher than expected level of C to T mutations in WRCG motifs at MC-1 and/or MC-3 sites in the non-transcribed strand (NTS) of a nucleic acid molecule from a biological sample is observed. TSM is also likely to have occurred if a higher than expected level of G to A mutations in CGYW motifs at MC-2 sites in the (TS) of a nucleic acid molecule from a biological sample is observed.

3.2 Apolipoprotein B mRNA-Editing Enzyme, Catalytic Polypeptide-Like (APOBEC) Cytidine Deaminases In addition to AID, the human genome encodes several homologous APOBEC cytidine deaminases that are known to be involved in innate immunity and RNA editing (Smith et al. (2012), *Semin. Cell. Dev. Biol.* 23: 258-268). In humans, at least APOBEC1, APOBEC3A, APOBEC3B, APOBEC3C, APOBEC3D, APOBEC3F, APOBEC3G and APOBEC3H are involved in providing innate immunity and/or cellular mRNA editing.

In some embodiments of the present invention, the cancer is an ovarian cancer (e.g., serous ovarian adenocarcinoma) and the biological sample comprises ovarian cells and/or tissue, APOBEC3B targets a motif comprising the nucleic acid sequence TCG/CGA. Specifically, TSM is likely to have occurred if a higher than expected level of C to T mutations in TCG motifs at MC-1 and/or MC-3 sites of a nucleic acid molecule from a biological sample is observed. In addition, TSM is likely to have occurred if a higher than expected level of G to A mutations in CGA motifs at MC-1 sites of a nucleic acid molecule from a biological sample is observed.

In some embodiments of the present invention, APOBEC3G targets a motif comprising the nucleic acid sequence CCG. Specifically, TSM is likely to have occurred if a higher than expected level of C to T mutations in CCG motifs at MC-1 sites of a nucleic acid molecule from a biological sample is observed.

In some embodiments of the present invention, APOBEC3G targets a motif comprising the nucleic acid sequence CGG. Specifically, TSM is likely to have occurred if a higher than expected level of G to A mutations in CGG motifs at MC-2 sites of a nucleic acid molecule from a biological sample is observed.

In other embodiments, the cancer is a leukaemia (e.g., acute myeloid leukaemia (AML)) and the biological sample comprises peripheral blood. In AML, increased TSM caused by an APOBEC isoform indicates an increased risk that the cancer will recur or progress. By way of an illustrative example of this type, TSM is likely to have occurred if a higher than expected level of at least one of the following mutations is observed in the nucleic acid molecule: C to T mutations in CCZ motifs at MC-1 sites; C to T mutations in SWCS motifs at MC-2 sites; G to A mutations in XNGNS motifs at MC-3 sites; G to A mutations in GSA motifs at MC-2 sites; G to A mutations in SGXW motifs at MC-1 sites; G to A mutations in CXGS motifs at MC-3 sites; G to A mutations in YXGNX motifs at MC-3 sites; G to A mutations in YYGNX motifs at MC-3 sites; and G to A mutations in WNGNZ motifs at MC-1 sites.

3.3 Adenosine Deaminases Acting on RNA (ADARs)

RNA editing is a post-transcriptional processing mechanism that results in an RNA sequence that is different from that encoded by the genomic DNA and thereby diversifies the gene product and function. The type of RNA editing that is most prevalent in higher eukaryotes converts adenosine residues into inosine (A-to-I editing) in double-stranded RNA (dsRNA) through the action of double-stranded RNA-specific adenosine deaminases, or ADAR, enzymes.

ADAR is an enzyme that is encoded by the ADAR gene in humans. The ADAR1 enzyme destabilizes dsRNA through conversion of adenosine to inosine. The ADAR1 enzyme modifies cellular and viral RNA, including coding and noncoding RNAs. ADAR1 is an RNA editing enzyme, required for hematopoiesis. ADAR1$^{+/-}$ chimeric embryos die before embryonic day 14 with defects in the hematopoietic system. Regulated levels of ADAR1 expression are critical for embryonic erythropoiesis in the liver. Mutations in the ADAR gene have been associated with dyschromatosis symmetrica hereditaria. Alternate transcriptional splice variants, encoding different isoforms, have been characterized.

In some embodiments of the present invention, wherein the cancer is an ovarian cancer (e.g., serous ovarian adenocarcinoma) and the biological sample comprises ovarian cells and/or tissue ADAR1 targets a motif comprising the nucleic acid sequence WAY. Specifically, TSM is likely to have occurred if a higher than expected level of A to G mutations in WAY motifs at MC-2 sites of a nucleic acid molecule from a biological sample is observed.

In some embodiments of this type, wherein the cancer is an ovarian cancer (e.g., serous ovarian adenocarcinoma) and the biological sample comprises ovarian cells and/or tissue, ADAR1 targets a motif comprising the nucleic acid sequence RAWA. Specifically, TSM is likely to have occurred if a higher than expected level of A to T mutations in RAWA motifs at MC-1 sites of a nucleic acid molecule from a biological sample is observed.

In some embodiments of the present invention, wherein the cancer is an ovarian cancer (e.g., serous ovarian adenocarcinoma) and the biological sample comprises ovarian cells and/or tissue, ADAR1 targets a motif comprising the nucleic acid sequence WTAW. Specifically, TSM is likely to have occurred if a higher than expected level of A to G mutations in WTAW motifs at MC-1 sites of a nucleic acid molecule from a biological sample is observed.

In some embodiments of the present invention, wherein the cancer is an ovarian cancer (e.g., serous ovarian adenocarcinoma) and the biological sample comprises ovarian cells and/or tissue, ADAR1 targets a motif comprising the nucleic acid sequence SARA. Specifically, TSM is likely to have occurred if a higher than expected level of A to G mutations in SARA motifs at MC-1 sites of a nucleic acid molecule from a biological sample is observed.

In some embodiments of the present invention, wherein the cancer is an ovarian cancer (e.g., serous ovarian adenocarcinoma) and the biological sample comprises ovarian cells and/or tissue, ADAR1 targets a motif comprising the nucleic acid sequence TWTY. Specifically, TSM is likely to have occurred if a higher than expected level of T to C mutations in TWTY motifs at MC-2 sites of a nucleic acid molecule from a biological sample is observed.

In some embodiments of the present invention, wherein the cancer is an ovarian cancer (e.g., serous ovarian adenocarcinoma) and the biological sample comprises ovarian cells and/or tissue, ADAR1 targets a motif comprising the nucleic acid sequence TWTY. Specifically, TSM is likely to have occurred if a higher than expected level of T to C mutations in TWTY motifs at MC-3 sites of a nucleic acid molecule from a biological sample is observed.

4. Methods for Detecting TSM

As demonstrated herein, some mutagenic agents not only cause mutagenesis of a nucleotide at one or more particular motifs, but the motif and mutated nucleotide are recognized within the codon context, i.e., the mutated nucleotide is at a particular position within the codon structure, such as the first, second or third nucleotide in the mutated codon (read 5' to 3'). There is also a clear preference for the replacement or substituting nucleotide. This combination of motif-specific, and codon context-specific, targeting by mutagenic agents is termed herein as TSM. By way of a non-limiting example, and as shown in Table 5, mutation of C at a WR CG motif in the non-transcribed strand of a nucleic acid molecule may preferentially occur at the first position of the mutated codon (MC-1) and be a mutation to T (i.e., C to T). Thus, the likelihood of whether or not targeted somatic mutation of a nucleic acid molecule has occurred can be determined by analysing the sequence of a nucleic acid molecule to determine the codon context of mutations of a mutation type (e.g., C to T) at one or more particular motifs (e.g., a WRCGSS motif). If there is no codon bias in the location of the mutations of the mutation type at the motif (i.e., the mutations are essentially evenly distributed across each position in the codons), then it is most likely that the mutations arose by chance and not as a result of TSM by a mutagenic agent. However, if there is a higher than percentage or number of mutations of the mutation type at one particular position in codons (e.g., MC-1, MC-2 or MC-3 sites) in the nucleic acid molecule, then this indicates that TSM has occurred or is likely to have occurred.

The "expected number or percentage" of the mutations described above is the number or percentage of mutations expected if the mutations are independent of other mutations and codon context, i.e., the distribution of mutations at each targeted nucleotide in each position in the codon is essentially even. Thus, for example, when assessing mutations arising across MC-1, MC-2 and MC-3 positions or sites, it would be expected that mutation of a nucleotide (e.g., C) to any one of the other three nucleotides (e.g., G, A or T) at any one of the three site (e.g., MC-1, MC-2 or MC-3) would occur as 1 in every 9 mutations (i.e., 1 in 3 chance of C to any one of G, A or T, and a 1 in 3 chance at any site, equaling a 1 in 9 chance overall) or approximately 11% of the time. When assessing mutations arising across just two of the nucleotide positions in the mutated codon, such as the MC-1 and MC-2 sites, it would be expected that mutation of a nucleotide (e.g., C) to any one of the other nucleotides (e.g., G, A or T) at either of the two sites (e.g., MC-1 or MC-2), would occur as 1 in every 6 mutations, or approximately 17% of the time (i.e., 1 in 3 chance of C to any one of G, A or T, and a 1 in 2 chance at any site, equaling a 1 in 6 chance overall). Similarly, when assessing mutations arising across just one of the sites (e.g., MC-1), it would be expected that mutation of a nucleotide (e.g., C) to any one of the other nucleotides (e.g., G, A or T) would occur as 1 in every 3 mutations, or approximately 33% of the time Typically, when TSM occurs as a result of the activity of one or more mutagenic agents and an assessment is made across the three sites of the codon (e.g., MC-1, MC-2 and MC-3), the particular mutations that are associated with the mutagenic agent are observed at least or about 20%, 25%, 30%, 35%, 40%, 45%, 50%, 55%, 60%, 65%, 70%, 75%, 80%, 85%, 90%, 95% or more of the time. When an assessment is made across at two sites (e.g., MC-1 and MC-2; MC-1 and MC-3; or MC-2 and MC-3), the particular mutations that are associated with the mutagenic agent are typically observed at least or about 30%, 35%, 40%, 45%, 50%, 55%, 60%, 65%, 70%, 75%, 80%, 85%, 90%, 95% or more of the time. When an assessment is made across only one site (e.g., MC-1; MC-2; or MC-3), the particular mutations that are associated with the mutagenic agent are typically observed at least or about 50%, 55%, 60%, 65%, 70%, 75%, 80%, 85%, 90%, 95% or more of the time.

4.1 TSM by AID, APOBECs and ADARs

As described above and elsewhere herein, in ovarian cancer AID has been found to specifically target the motif WRCG/CGYW, wherein the underlined nucleotide is mutated. As demonstrated herein, there is a significant preference for targeting of the G to occur at MC-2 sites, resulting in G to A mutations. Accordingly, a higher than expected number or percentage of G to A mutations at CGYW motifs at MC-2 sites of a nucleic acid molecule indicates that AID is a likely cause of TSM of the nucleic acid, and that AID is active in the ovarian cells and/or tissue from which the biological sample was obtained. As also demonstrated herein, and again using ovarian cancer as a non-limiting example, there is a significant preference for targeting of the C to occur at MC-1 sites, resulting in C to T mutations. Accordingly, a higher than expected number or percentage of C to T mutations at WRCG motifs at MC-1 sites of a nucleic acid molecule indicates that TSM of the nucleic acid has likely occurred, and that AID is likely to be active in the cells and/or tissue from which the nucleic acid molecule was obtained.

Also in ovarian cancer APOBEC3G is has been found to specifically target CGG/CCG motifs. The studies described herein demonstrate that there is a significant preference for targeting of the G to occur at MC-2 sites, resulting in G to A mutations. Accordingly, a higher than expected number or percentage of G to A mutations at CGG motifs at MC-2 sites of a nucleic acid molecule indicates that TSM of the nucleic acid has likely occurred, and that APOBEC3G is likely to be active in the cells and/or tissue from which the nucleic acid was obtained. There is also a significant preference for targeting of the C to occur at MC-1 and/or MC-3 sites, resulting in C to T mutations. Accordingly, a higher than expected number or percentage of C to T mutations at CCG motifs at MC-1 and/or MC-3 sites of a nucleic acid molecule indicates that somatic mutagenesis of the nucleic acid has likely occurred, and that APOBEC3G is likely to be active in the cells and/or tissue from which the nucleic acid molecule was obtained.

APOBEC3B has been found to specifically target TCG/CGA motifs in ovarian cancer samples. The studies described herein demonstrate that there is a significant preference for targeting of the C to occur at MC-1 and/or MC-3 sites, resulting in C to T mutations. Accordingly, a higher than expected number or percentage of C to T mutations at TCG motifs at MC-1 and/or MC-3 sites of a nucleic acid molecule indicates that TSM of the nucleic acid has likely occurred, and that APOBEC3B is likely to be active in the cells and/or tissue from which the nucleic acid molecule was obtained. There is also a significant preference for targeting of the G to occur at MC-1 sites, resulting in G to A mutations. Accordingly, a higher than expected number or percentage of C to T mutations at CGA motifs at MC-1 sites of a nucleic acid molecule molecule indicates that somatic mutagenesis of the nucleic acid has likely occurred, and that APOBEC3B is likely to be active in the cells and/or tissue from which the nucleic acid molecule was obtained.

Finally, ADAR1 is known to target WAY motifs in ovarian cancer. The studies described herein demonstrate that there is a significant preference for targeting of the A to occur at MC-2 sites, resulting in A to G mutations. Accordingly, a higher than expected number or percentage of A to G mutations at WAY motifs at MC-2 sites in the non-transcribed strand of a nucleic acid molecule indicates that TSM of the nucleic acid has likely occurred, and that ADAR is likely to be active in the cells and/or tissue from which the nucleic acid molecule was obtained.

4.2 Identifying Motifs for Other Mutagenic Agents

As clearly demonstrated herein, mutagenic agents may target a nucleotide in a motif within a particular codon context. Thus, targeted somatic mutation by such agents generally results in one type of mutation (e.g., C to T, and not C to G or C to A), at one position within the codon structure (e.g., MC-1 and not MC-2 or MC-3) and at one motif (e.g., CCG). By analysing nucleic acid sequences for the particular mutation type at the motif and within a particular codon context, as described above, a more accurate indication of whether TSM has occurred than if just the incidence of mutations at the motif were to be examined.

This bias for codon context can be used to identify motifs for other mutagenic agents. By analysing a nucleic acid molecule for the incidence of somatic mutations of a mutation type known to be associated with a mutagenic agent (e.g., G to T), and also assessing the codon context of the mutations and the nucleotides flanking the mutation, the motif for the mutagenic agent may be identified. When a particular mutation (e.g., G to T) occurs at a particular position within a codon (e.g., MC-3) more frequently than would occur at random, i.e., there is a preferred nucleotide position at which the mutation occurs, then it is likely that the mutations at this position occur as a result of targeted somatic mutation by the mutagenic agent. By analysing the nucleotides flanking the mutation at the preferred nucleotide position (e.g., MC-3), any motif common to the mutations and thus targeted by the mutagenic agent can be identified.

Thus, the present invention also provides methods for identifying a motif targeted by a mutagenic agent. The methods involve analysing the sequence of a nucleic acid molecule to determine whether a mutation type associated with the mutagenic agent predominantly occurs at one position or site of a codon (e.g., MC-1, MC-2 or MC-3). If there is a co-incidence of mutation type and site, then the nucleotides flanking the mutated nucleotide are identified so as to identify a common motif that includes the mutated nucleotide. More specifically, the methods involve analysing the sequence of a nucleic acid molecule to identify somatic mutations of a mutation type known to be associated with the mutagenic agent, determining the codon context of the mutations to identify a preferred nucleotide position at which the mutations occur at a higher than expected frequency, and identifying the nucleotides flanking the mutations at the preferred nucleotide position so as to identify a motif that is common to the mutations.

A similar process can also be applied when the mutation type associated with a mutagenic agent is not yet known. In such cases, the sequence of a nucleic acid molecule is first analysed to identify somatic mutations, and any mutation type (e.g., G to T) that occurs at a position within a codon (e.g., MC-3) at a frequency that is higher than expected if the mutation occurred randomly (i.e., at a preferred nucleotide position) are also identified. The sequence flanking the mutation at the preferred nucleotide position is then assessed to determine whether there is a motif that is common to the mutation. If there is, this motif is likely the target of the mutagenic agent.

In other examples, known motifs of mutagenic agents can be further analysed to determine the codon bias and preference for a mutation type. Nucleic acid sequences can be assessed as described herein, such as in Example 1, to determine the codon context and mutation type associated with mutations at the motif so as to assess whether there is a preference for a mutation type at a nucleotide position in the codon. For example, APOBEC3A, APOBEC3B, APOBEC3F and APOBEC3H are thought to target a TC motif, or a more stringent TCW motif. The sequence of one or more nucleic acid molecules can be analysed to determine the codon context in which mutations at the motif occur, i.e., whether the C is at MC-1, MC-2 or MC-3, and what type of mutation occurs, (e.g., C to A, C to T, or C to G). Once the co-incident mutation type, motif and codon context are identified, this set of criteria, or diagnostic rule, can be used to more accurately determine whether TSM has occurred in a nucleic acid molecule, and thus also determine what mutagenic agents are active in the cells from which the nucleic acid molecule was obtained.

To identify motifs and/or diagnostic rules using the methods described above, the nucleic acid molecule that is analysed is typically a nucleic acid that is known or suspected to have been in contact with the mutagenic agent or is nucleic acid that has been obtained from cells that are known or suspected to have been in contact with the mutagenic agent. For example, cells comprising the nucleic acid molecule may be exposed in vitro to the mutagenic agent before nucleic acid sequence is analysed. In other examples, the nucleic acid molecule may be obtained from tissue or cells from subjects that are known to have been exposed to the mutagenic agent. Multiple studies using multiple biological samples may be performed to validate the findings.

4.3 Identifying Motifs for Other Tissue Types

As shown in the examples, the DBDs characterized for an individual deaminase isoform is specific for a particular tissue type. Thus, a prediction of the level of TSM in a biological sample obtained from a one particular tissue type is specific only for that tissue type. Thus, in preferred embodiments TSM motifs are identified in a biological sample derived from tissue that is known to be affected by cancer, and compared to the corresponding healthy tissue (e.g., tissue in which cancer is known to be absent, and not at risk of developing cancer).

By way of an example, the biological sample may comprise tissue, blood, and/or cells. In some examples, the biological sample is a biopsy. Moreover, the biological sample may from any part of the body and may comprise any type of cells or tissue, such as, for example, breast, prostate, liver cells, colon, stomach, pancreatic, skin, thyroid, cervical, lymphoid, hematopoietic, bladder, lung, renal, rectal, ovarian, uterine, and head or neck tissue or cells, or cells from peripheral blood or cerebrospinal fluid. In some instances, the nucleic acid molecule is obtained from a cell or tissue sample from a subject suspected of or at risk of having cancer, or is obtained from a cell or tissue sample from a subject that has cancer.

4.4 Assessing the Nucleic Acid Molecule for TSM

Any method known in the art for obtaining and assessing the sequence of a nucleic acid molecule can be used in the methods of the present invention. The nucleic acid molecule analysed using the methods of the present invention can be any nucleic acid molecule, although is generally DNA (including cDNA). Typically, the nucleic acid molecule is mammalian nucleic acid molecule, such as human nucleic acid molecule. As described above, the nucleic acid molecule can be obtained from any biological sample.

The nucleic acid molecule can contain a part or all of one gene, or a part or all of two or more genes, and it is the sequence of this gene or genes that is analysed according to the methods of the invention. For example, the nucleic acid molecules may comprise all or part of the TP53, PIK3CA, ERBB2, DIRAS3, TET2 or nitric oxide synthase (NOS) genes. In some instances, the nucleic acid molecule comprises the whole genome or whole exome, and it is the sequence of the whole genome or whole exome that is analysed in the methods of the invention.

When using the methods of the present invention, the sequence of the nucleic acid molecule may have been predetermined. For example, the sequence may be stored in a database or other storage medium, and it is this sequence that is analysed according to the methods of the invention. In other instances, the sequence of the nucleic acid molecule must be first determined prior to employment of the methods of the invention. In particular examples, the nucleic acid molecule must also be first isolated from the biological sample.

Methods for obtaining nucleic acid and/or sequencing the nucleic acid are well known in the art, and any such method can be utilized for the methods described herein. In some instances, the methods include amplification of the isolated nucleic acid prior to sequencing, and suitable nucleic acid amplification techniques are well known to a person of ordinary skill in the art. Nucleic acid sequencing techniques are well known in the art and can be applied to single or multiple genes, or whole exomes or genomes. These techniques include, for example, capillary sequencing methods that rely upon 'Sanger sequencing' (Sanger et al., (1977) Proc. Natl. Acad. Sci. USA 74: 5463-5467) (i.e., methods that involve chain-termination sequencing), as well as "next generation sequencing" techniques that facilitate the sequencing of thousands to millions of molecules at once. Such methods include, but are not limited to, pyrosequencing, which makes use of luciferase to read out signals as individual nucleotides are added to DNA templates; "sequencing by synthesis" technology (Illumina), which uses reversible dye-terminator techniques that add a single nucleotide to the DNA template in each cycle; and SOLID™ sequencing (Sequencing by Oligonucleotide Ligation and Detection; Life Technologies), which sequences by preferential ligation of fixed-length oligonucleotides. These next generation sequencing techniques are particularly useful for sequencing whole exomes and genomes.

Once the sequence of the nucleic acid molecule is obtained, single point somatic mutations are then identified. Single point mutations may be identified by comparing the sequence to a control sequence. The control sequence may be the sequence of a nucleic acid molecule obtained from a biological sample from a control individual, such as a healthy individual that is free of disease; the sequence of a nucleic acid molecule obtained from a control sample, such as a sample from healthy, non-diseased tissue; or may be a consensus sequence understood to contain no somatic mutations. In some instances, the control sequence may be a sequence of a nucleic acid molecule obtained from a biological sample from the subject at a previous point in time. For example, the control sample can be taken before or during the subject being exposed to a treatment regimen, and the sample to be analysed may be post-treatment (to determine whether the subject is responding to treatment, and to determine the likelihood of a cancer or tumour recurring). In addition to identify the single point mutations, the codon containing the mutation and the position of the mutation within the codon (MC-1, MC-2 or MC-3) is identified. Nucleotides in the flanking 5' and 3' codons are also identified so as to identify the motifs. Typically, for the methods of the present invention, the sequence of the non-transcribed strand (equivalent to the cDNA sequence) of the nucleic acid molecules is analysed). In some instances, the sequence of the transcribed strand is analysed.

As demonstrated herein, using the methods of the present invention, only a small number of mutations at motifs need be analysed to determine with statistical significance whether TSM has occurred as a result of the activity of particular mutagenic agent. In some instances, the number of mutations at a particular motif analysed using the methods of the present invention may be as few as 2 mutations. For example, if it is found that an apparently healthy patient has only 2 somatic mutations in the analysed nucleic acid, and both of these are G to A mutations in a GYW motif at an MC-2 site, then the probability that this pattern arose by chance is 0.04238 (p<95%, using a ChiSquare test, 9−1=9 df). Alternatively, the probability of each of the mutations occurring by chance can be said to be 1/9 (i.e., a 1/3 chance of a G to A mutation, and a 1/3 chance of the mutation being at an MC-2 sites, as discussed above), and the probability that 2 out of 2 mutations occur in this pattern is therefore 1/81 (or 0.012346). However, as would be understood by those skilled in the art, statistical significance may be improved when more mutations at a particular motif analysed. Thus, in some instances, the number of mutations at a particular motif analysed using the methods of the present invention may be at least 20. Many nucleic acid-containing biological samples from subjects before or after treatment have 40 or more mutations, with some harbouring up to 400 or more mutations. Accordingly, the number of mutations at a particular motif analysed using the methods of the present invention may be at least or about 2, 3, 4, 5, 6, 7, 8, 9, 10, 15, 20, 25, 30, 40, 50, 60, 70, 80, 90, 100, 150, 200, 250, 300 or more.

5. Cancer-Progression Associated Markers (C-PAS)

The present invention also discloses that a subset of TSM is associated with the likelihood of cancer recurrence (herein referred to as "Cancer-Progression Associated Signatures;" (C-PAS)). C-PAS can be identified by detecting individual nucleic acid sequences that are specifically targeted by mutagenic agents (e.g., AID, APOBECs, ADARs, etc.), and are indicative of the recurrence of cancer.

5.1 Identifying C-PAS

In some embodiments, the invention includes the identification of C-PAS in a nucleic acid that is present in a biological sample from a subject that has or has had a cancer. Two rules can be met to be considered as a C-PAS. First, the single nucleotide substitution by the mutagenic agent identified in the C-PAS must show a significant targeting preference (i.e., be of a single type and codon context). This ensures that the nucleic acid motif is associated with the mutagenic activity of a single deaminase, and that the resulting TSM pattern (i.e., C-PAS) does not arise by chance alone. The second criteria for a nucleic acid motif to be considered as a C-PAS is that there must be an increase in the average number of targeted mutations per sample in the C-PAS between samples from cancers that recur, and those that do not recur.

Thus, the methods for identifying C-PAS involve analysing the sequence of a nucleic acid molecule to determine whether a mutation type associated with the mutagenic agent predominantly occurs at one position or site of a codon (e.g., MC-1, MC-2 or MC-3). If there is a co-incidence of mutation type and site, then the nucleotides flanking the mutated nucleotide are identified so as to identify a common motif that includes the mutated nucleotide. More specifically, the methods involve analysing the sequence of a nucleic acid molecule to identify somatic mutations of a mutation type known to be associated with the mutagenic agent, determining the codon context of the mutations to identify a preferred nucleotide position at which the mutations occur at a higher than expected frequency, and identifying the nucleotides flanking the mutations at the preferred nucleotide position so as to identify a motif that is common to the mutations. Analysis is then performed to determine whether the TSM in the C-PAS is capable of distinguishing between a cancer that is likely to recur and a cancer that is not likely to recur, using methods that are well known in the art for determining statistical significance.

To identify motifs and/or diagnostic rules using the methods described above, the nucleic acid that is analysed is typically a nucleic acid that has been obtained from cells or tissues from a subject that is known or suspected to have a cancer that has recurred, or to have previously had a cancer that has not recurred. Multiple studies using multiple biological samples may be performed to validate the findings.

To this extent, and by way of a non-limiting illustrative example of C-PAS that are suitable for determining the likelihood of a cancer (e.g., ovarian cancer, AML, etc.) recurring in a subject, is provided in Table 3.

TABLE 3

Identified C-PAS and Codon Context

| Tissue Type | Mutagenic Agent | C-PAS | Mutation Type | Codon Site |
|---|---|---|---|---|
| Ovarian | AID | WRC GSS | C to T | MC-1 |
|  | APOBEC3B | TCG A | C to T | MC-1 |
|  |  | ATC S | C to T | MC-3 |
|  | APOBEC3G | GC GGC | C to T | MC-1 |
|  |  | CC GX | C to T | MC-1 |
|  |  | ZCC G | C to T | MC-1 |
|  |  | SG GRR | G to A | MC-1 |

TABLE 3-continued

Identified C-PAS and Codon Context

| Tissue Type | Mutagenic Agent | C-PAS | Mutation Type | Codon Site |
|---|---|---|---|---|
| | | TCC G | C to T | MC-1 |
| | | GCG C | G to A | MC-2 |
| | | CCG GC | G to A | MC-2 |
| | ADARs | RAWA | A to T | MC-1 |
| | | WTA W | A to G | MC-1 |
| | | SARA | A to G | MC-1 |
| | | T WTY | T to C | MC-2, MC-3 |
| AML | APOBECs | CC Z | C to T | MC-1 |
| | | SWC S | C to T | MC-2 |
| | | XNG NS | G to A | MC-3 |
| | | G SA | G to A | MC-2 |
| | | SG XW | G to A | MC-1 |
| | | CXG S | G to A | MC-3 |
| | | YXG NX | G to A | MC-3 |
| | | YYG NX | G to A | MC-3 |
| | | WNG NZ | G to A | MC-1 |

The specific identification and characterization of C-PAS allows for a fast determination as to whether TSM has occurred in a nucleic acid molecule. Furthermore, by further defining the sites that are specifically targeted by a mutagenic agent (e.g., deaminase) it is expected that a higher specificity and sensitivity of determining the likelihood that a cancer will recur in a subject will result. In this regard, the identification and characterisation of the C-PAS must be performed in the specific tissue sample of the cancer to be assessed. As shown in Table 3, distinct C-PAS are identified in each tissue type or cancer of interest, and these sequences cannot be predicted prior to performing the C-PAS identification methods described herein.

As an illustrative example of the methods described above and elsewhere herein, if the level of TSM in a C-PAS in a nucleic acid is determined to be higher than what would be expected if random (i.e., non-targeted) mutagenesis has occurred then it is likely that a cancer will recur in a subject. Conversely, if the level of TSM in a C-PAS is similar to or below what would be expected if random (i.e., non-targeted) mutagenesis has occurred it is likely that a cancer or tumour will not recur in a subject.

6. Kits and Systems for Detecting TSM and C-PAS

All the essential materials and reagents required for detecting TSM in a subject and further identifying the likelihood that cancer or tumour is likely to recur, and related methods as described herein, may be assembled together in a kit. For example, when the methods of the present invention include first isolating and/or sequencing the nucleic acid to be analysed, kits comprising reagents to facilitate that isolation and/or sequencing are envisioned. Such reagents can include, for example, primers for amplification of DNA, polymerase, dNTPs (including labelled dNTPs), positive and negative controls, and buffers and solutions. Such kits will also generally comprise, in suitable means, distinct containers for each individual reagent. The kit can also feature various devices, and/or printed instructions for using the kit.

In some embodiments, the methods described generally herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to identify mutation types, the codon context of a mutation and/or motifs within one or more nucleic acid sequences. In some examples, commands inputted to the processing system by a user assist the processing system in making these determinations.

In one example, a processing system includes at least one microprocessor, a memory, an input/output device, such as a keyboard and/or display, and an external interface, interconnected via a bus. The external interface can be utilised for connecting the processing system to peripheral devices, such as a communications network, database, or storage devices. The microprocessor can execute instructions in the form of applications software stored in the memory to allow the methods of the present invention to be performed, as well as to perform any other required processes, such as communicating with the computer systems. The applications software may include one or more software modules, and may be executed in a suitable execution environment, such as an operating system environment, or the like.

Figure 3:
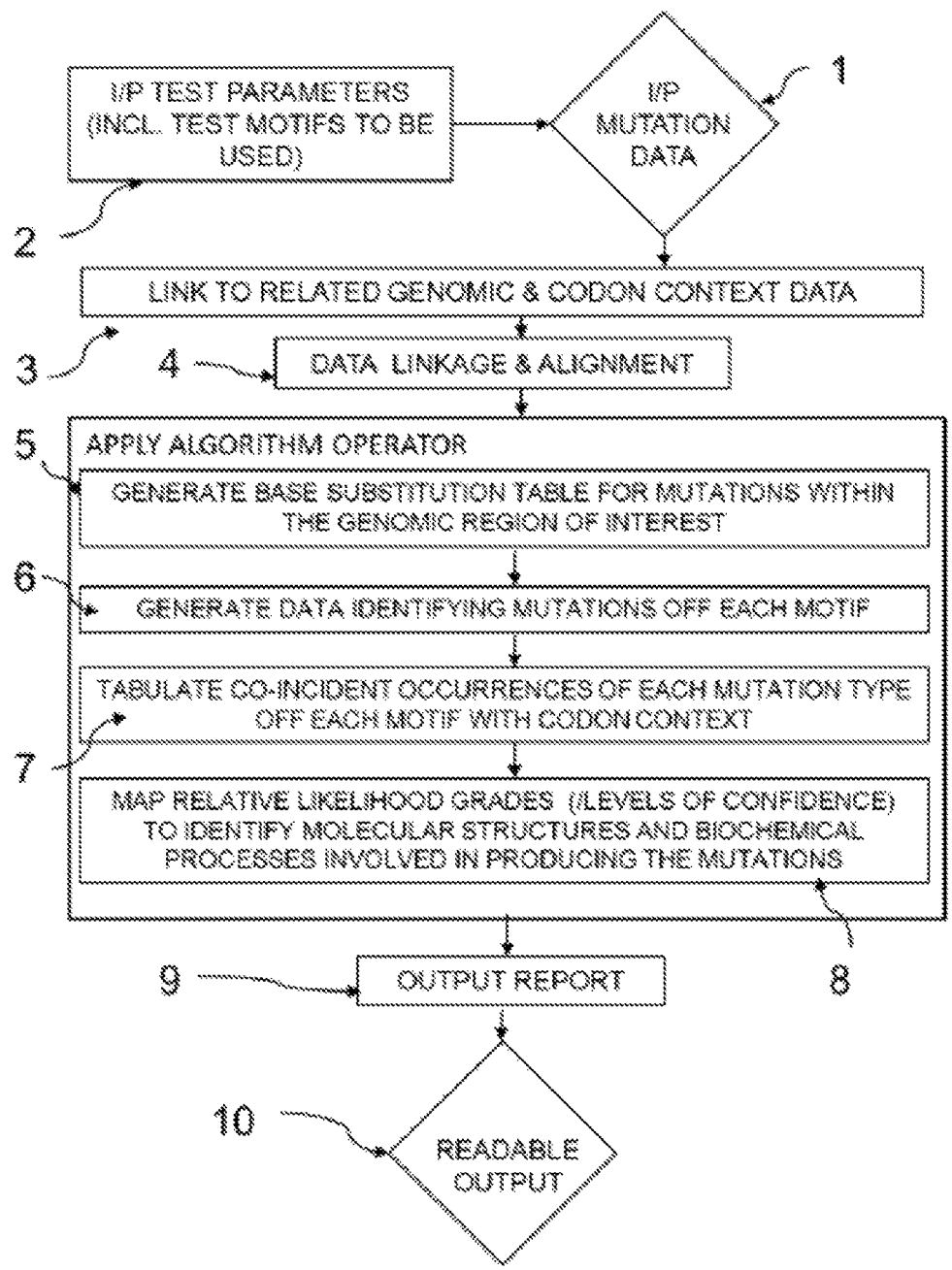
FIG. 3 is a schematic of the process of detecting targeted somatic mutagenesis in a nucleic acid molecule using a process system.

In another example, the processing system can be used to upload sequence information and other relevant data from databases or other sources. Algorithms devised to be appropriate for the methods disclosed herein can be applied to data, such as shown in FIG. 3. In this example, input data [1] and test parameters (such as motifs to be used) [2] are uploaded or entered into the system. A base substitution table is then generated for mutations within the genomic region of interest with data aligned and linked to mutations with codon context data and other information linked to sample details and nucleotide sequence [3, 4, 5]. The next step involves the identification of co-incident occurrences of each mutation type at each motif at each nucleotide position within the codons [6]. The data are tabulated to record co-incident occurrences of each mutation type off each motif with codon context [7], including the relative likelihood grades with levels of confidence for each diagnosis [8]. The results are linked to identify the mutagenic agents (or molecular structures) and the biochemical processes likely to be involved in producing the mutations and relevant clinical information [8]. An output report is generated according to the service request information used as input [9] and a readable output is generated [10].

7. Diagnostic and Therapeutic Applications

The methods described herein for detecting whether targeted somatic mutagenesis has occurred, and the identification and characterization of C-PAS, have many useful diagnostic and therapeutic applications. Somatic mutagenesis is known to be associated with the presence of many cancers. Similarly, some mutagenic agents are known to be associated with the development and progression of many cancers. Using the methods described herein (e.g., the presence and/or extent of TSM resulting from one or more mutagenic agents), the likelihood of a cancer recurring in a subject can be determined. Such a determination can facilitate the prescribing of a treatment regimen for a subject who has or has had cancer For example, the determination can assist with deciding whether the current treatment regimen should continue, be reduced or be stopped. In addition, ongoing assessment of targeted somatic mutations attributable to one or more mutagenic agents can be used to assess whether a cancer is progressing or regressing and/or the success or failure of a treatment regimen. For example, an increase in the number of targeted somatic mutations detected in nucleic acid from a sample, such as a biopsy, over time in the same subject can indicate a worsening of the cancer or a failure to respond to a treatment regimen, while a stabilization or reduction in the number of mutations can indicate remission of the condition or a successful response to a treatment regimen.

In particular instances, the methods of the present invention can extend to the diagnosis of cancer in a subject or a determination of the likelihood that a cancer will recur in a subject. For example, the likelihood that a cancer will recur in a subject can be assessed by analysing a nucleic acid molecule from a biological sample from the subject so as to determine whether TSM by one or more mutagenic agents has occurred. If TSM has occurred, a determination can be made that the cancer is likely to recur in the subject.

In some examples, the diagnostic rules described above are utilized to determine the likelihood that a cancer will recur in a subject. For example, a cancer will be determined to be likely to recur when the number or percentage of observed C to T mutations in TCGA motifs at MC-1 sites of a nucleic acid molecule is higher than expected; the number or percentage of observed C to T mutations in ATCS motifs at MC-3 sites of a nucleic acid molecule is higher than expected; the number or percentage of observed C to T mutations in GCGGC motifs at MC-1 sites of a nucleic acid molecule is higher than expected; the number or percentage of observed C to T mutations in CCGX motifs at MC-1 sites of a nucleic acid molecule is higher than expected; the number or percentage of observed C to T mutations in ZCCG motifs at MC-1 sites of a nucleic acid molecule is higher than expected; the number or percentage of observed G to A mutations in SGGRR motifs at MC-1 sites of a nucleic acid molecule is higher than expected; the number or percentage of observed C to T mutations in TCCG motifs at MC-1 sites of a nucleic acid molecule is higher than expected; the number or percentage of observed G to A mutations in GCGC motifs at MC-2 sites of a nucleic acid molecule is higher than expected; the number or percentage of observed G to A mutations in CCGGC motifs at MC-2 sites of a nucleic acid molecule is higher than expected; the number or percentage of observed; the number or percentage of observed A to T mutations in RAWA motifs at MC-1 sites of a nucleic acid molecule is higher than expected; the number or percentage of observed A to G mutations in WTAW motifs at MC-1 sites of a nucleic acid molecule is higher than expected; the number or percentage of observed A to G mutations in SARA motifs at MC-1 sites of a nucleic acid molecule is higher than expected; the number or percentage of observed T to C mutations in TWTY motifs at MC-2 sites of a nucleic acid molecule is higher than expected; and/or the number or percentage of observed T to C mutations in TWTY motifs at MC-3 sites of a nucleic acid molecule higher than expected, as described above for AID, APOBEC3G, APOBEC3H and ADARs. In other examples, diagnostic rules determined for other mutagenic agents using the methods described herein are used to detect the likelihood of that a cancer will recur in a subject.

In some instances, when targeted somatic mutations are detected in a sample containing cells or tissue from a particular region or location in a subject, such as breast, prostate, liver, colon, stomach, pancreatic, skin, thyroid, cervical, lymphoid, haematopoietic, bladder, lung, renal, rectal, ovarian, uterine, and head or neck tissue or cells, then a determination that the subject has or is likely to develop cancer involving that tissue or those cells is made. Thus, for example, a determination that the subject has or is likely to develop breast, prostate, liver, colon, stomach, pancreatic, skin, thyroid, cervical, lymphoid, haematopoietic, bladder, lung, renal, rectal, ovarian, uterine, or head and neck cancer may be made.

In particular examples, the biological sample used to detect the likelihood of a specific type of cancer recurring is matched to the type of cancer. By way of an illustration, is the subject suffers from or has suffered from an ovarian cancer, then the sample on which the TSM is identified is derived from ovarian tissue or cells.

As well as being of use to determine the likelihood cancer recurrence, the extent of TSM (i.e., the total number of targeted somatic mutations attributable to the mutagenic agent in the nucleic acid) can also be used to assist in determining whether the cancer is progressing or regressing, and/or whether a treatment regimen is working or not. As described above, the higher the number of TSM, the higher the likelihood that the cancer will recur in the subject. Furthermore, if there is an increase in the number of targeted somatic mutations over time in a subject, the higher the likelihood that the cancer is progressing and/or the subject is not responding to the cancer or tumour. Conversely, if there is a decrease in the number of targeted somatic mutations over time in a subject, the higher the likelihood that the cancer is regressing and/or the subject is successfully responding to the treatment regimen.

The methods of the present invention also extend to therapeutic or preventative protocols. In instances where a cancer is determined to be unlikely to recur, protocols may be amended to reduce the intensity of the treatment, or to remove a subject from a treatment regimen completely. In instances where a cancer is determined to be likely to recur, protocols designed to reduce that likelihood may be designed and applied to a subject. For example, an appropriate therapeutic protocol can be designed for the subject and administered. This may include, for example, radiotherapy, surgery, chemotherapy, hormone ablation therapy, pro-apoptosis therapy and/or immunotherapy. In some examples, further diagnostic tests may be performed to confirm the diagnosis prior to therapy.

Radiotherapies include radiation and waves that induce DNA damage for example, γ-irradiation, X-rays, UV irradiation, microwaves, electronic emissions, radioisotopes, and the like. Therapy may be achieved by irradiating the localized tumour site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

Chemotherapeutic agents may be selected from any one or more of the following categories:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyridines like 5-fluorouracil and tegafur, raltitrexed, methotrexate, cytosine arabinoside and hydroxyurea; anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and docetaxel; and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (for example the anti-vascular endothelial cell growth factor antibody bevacizumab [AVASTIN™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Immunotherapy approaches, include for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

In some instances, where the likely identity of the mutagenic agent causing the targeted somatic mutations is determined, therapy or preventative measures may include administration to the subject of an inhibitor of that mutagenic agent. Inhibitors can include, for example, siRNAs, miRNAs, protein antagonists (e.g., dominant negative mutants of the mutagenic agent), small molecule inhibitors, antibodies and fragments thereof. For example, commercially available siRNAs and antibodies specific for APOBEC cytidine deaminases and AID are widely available and known to those skilled in the art. Other examples of APOBEC3G inhibitors include the small molecules described by Li et al. (*ACS. Chem. Biol.*, (2012) 7(3): 506-517), many of which contain catechol moieties, which are known to be sulfhydryl reactive following oxidation to the orthoquinone. APOBEC1 inhibitors also include, but are not limited to, dominant negative mutant APOBEC1 polypeptides, such as the mul (H61K/C93S/C96S) mutant (Oka et al., (1997) *J. Biol. Chem.* 272: 1456-1460).

Typically, therapeutic agents will be administered in pharmaceutical compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of cancer, and/or the reduction, regression or elimination of tumours or cancer cells. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner, and those of skill in the art may readily determine suitable dosages of the therapeutic agents and suitable treatment regimens without undue experimentation.

The present invention can be practiced in the field of predictive medicine for the purposes of diagnosis or monitoring the presence or development of a cancer or tumour in a subject, and/or monitoring response to therapy efficacy.

In order that the invention may be readily understood and put into practical effect, particular preferred embodiments will now be described by way of the following non-limiting examples.

EXAMPLES

Example 1

Mutation Strand-Bias Pattern Resembles Other Cancers

Previous studies have shown that the somatic hypermutation (SHM) reference pattern observed at rearranged immunoglobulin variable region loci is characterized by significant strand-biases evident for all Watson-Crick complements (see, for example, Steele and Lindley, 2010). The present studies provide the first evidence that the striking SHM-like strand biased pattern is also observed for somatic mutations occurring in lung adenocarcinoma, lung small cell carcinoma, breast ductal carcinoma, squamous cell carcinoma, and malignant melanoma. Accordingly, it was determined whether the strand-bias pattern for the TCGA serous ovarian adenocarcinoma mutation dataset also exhibited this strand bias. The results strongly suggest that there is a causal relationship between aberrant Ig SHM and the genesis of somatic point mutations in many cancers. This in turn suggests that the potential targets involved in SHM such as AID and ADAR1, and the processes modulating the transcription coupled repair (TCR) pathways are involved.

The strand bias mutation data shown in Table 4 is strikingly similar in part, or in toto, to the strand bias patterns for a rage of other cancers occurring in non-lymphoid tissues. That is, the likely root cause of the mutations observed in serous ovarian adenocarcinomas is the same as that observed for mutations in tumours of other somatic tissues. The results provide a qualified justification for adopting a targeted somatic mutation (TSM) approach involving the AID/APOBEC and ADAR families of deaminases to analyse the mutation data for the selected 194 serous ovarian adenocarcinoma samples.

TABLE 4

Patterns of somatic mutations in exome mutations

| To | A | T | C | G | Total |
|---|---|---|---|---|---|
| From A | — | 5.2 | 3.5 | 7.1 | 15.8 |
| T | 3.7 | — | 4.8 | 3.0 | 11.5 |
| C | 8.8 | 16.8 | — | 9.2 | 34.8 |
| G | 17.6 | 10.4 | 9.8 | — | 37.8 |
| | | | | | 100 |

Materials and Methods

Data Source

Somatic mutation data was sourced from a cohort of 429 clinically annotated stage II-IV serous ovarian adenocarcinoma samples archived by The Cancer Genome Atlas (TCGA 2013). A previous analysis of these samples by Kanchi et al (2014) was the first large-scale study using exome-wide sequencing of matched germline and tumour tissue samples.

The source of tumour and germline tissue is indicated by the code following the third hyphen in TCGA-XX-XXX-YYY-ZZZ (Cancer Genome Atlas Research Network, 2013). For example, the following codes in the area of YYY indicate the source as follows: 10 indicates Blood Derived Normal; 11 indicates Solid Tissue Normal; and 12 indicates Buccal Cell Normal. Many of the original samples were amplified prior to sequencing. The letter code in place of ZZZ indicates the amplification methods used. For example, D indicates DNA (no whole genome amplification); G indicates Whole Genome Amplification (WGA) produced using GENOMEPLEX (RUBICON) DN; and W indicates Whole Genome Amplification (WGA) produced using REPLI-G (QIAGEN) DNA.

DNA was sequenced by exome capture followed by sequencing on Illumina or SOLiD platforms. Sequence data from paired tumour and germline samples were aligned to NCBI Build 36 of the human reference using BWA 0.5.9, and de-duplicated using PICARD 1.29 (see, methods section in Kanchi et al., 2014).

Sample Selection

The DNA mutation data was analysed using an Educational Research In Codon-context (ERIC) Version 1.6. This application was developed as a research support tool. It is written in EXCEL VBA scripting to automate the process of analysing and compiling the DNA mutation data for analysis. The program routine uses the ENSEMBL gene transcripts (Cunningham et al., 2015) to identify the nucleotide sequence context surrounding each mutation, and to determine the position of each mutation within the nucleotide structure of the mutated codon (MC).

Once this data was added to the compiled mutation dataset, ERIC was then used to call and tabulate mutations falling on predefined motifs of interest and consisting of 3-6 nucleotides. Once the nucleotides of a selected motif are entered into the configuration settings, tables for all mutations off the selected motif are then tabulated to reveal the distribution of mutations within a 3×3 TSM table (see, Lindley 2013). The resulting TSM table shows the distribution of mutations (e.g., G to A, G to C or G to T), and their position with respect to the three possible nucleotide positions within the mutated codon (i.e., positions MC-1, MC-2, or MC-3 read 5' to 3').

Data Analysis

As a first step, strand-bias mutation analyses was performed on the pooled mutation dataset. The strand-bias pattern was then compared with the strand-bias patterns of a range of cancers in other tissue types. The strand-bias mutation pattern for the pooled data was created by tabulating the relative percentages of each type of mutation in a 4×4 table format (as described in Steele and Lindley, 2010; and Lindley and Steele, 2013).

Once the strand-bias mutation data pattern was analysed, the next step is to verify that the AID/APOBEC3G/APOBEC3B and ADAR families of deaminases are the likely source of many of the mutations. To complete this step, TSM tables for motifs previously found to be associated with key deaminases were tabulated. Non-overlapping targeting preferences ('motifs') include WR$\underline{C}$G/$\underline{CG}$YW for AID, and C$\underline{C}$G/$\underline{C}$GG for APOBEC3G (see, Beale, 2004). For ADAR activity, the motif WAY is selected, and for APOBEC3B, the motif T$\underline{C}$G/$\underline{C}$GA is used (see, Burns et al., 2013a). It should be noted that the APOBEC3B mutations have previously been shown to be significantly upregulated in serous ovarian carcinoma, and that several preferred trinucleotide target motifs have been identified in serous ovarian carcinoma (see, Leonard et al., 2013).

As all AID/APOBEC/ADAR family members are known to have multiple active DBDs, the chimeric nature of the key deaminases was verified using the following investigative approach.

This was done by first analysing the influence of changes in the 5 prime (5') and 3 prime (3') nuclear context starting with the AID preferred target motif on the transcribed strand (TS) of GYW. Using ERIC v.1.6, and starting with the trinucleotide motif GYW, we incrementally increased the number of nucleotides from three nucleotides to six nucleotides. For each extension, we selected additional nucleotides that did not alter the targeting preference within the structure of the mutated codon, or the resulting dominant type of mutation.

Second, a table was constructed to investigate how changes in the 5 prime (5') and 3 prime (3') context of the targeting preferences for different motifs for AID and ADAR families might alter either or both the type of mutation, and the preferred target site of mutations within the trinucleotide structure of the mutated codon. This is to investigate the polymorphic nature of these deaminases, and to understand how changes in the 5 prime (5') or 3 prime (3') nucleotide context might alter the preferred target sites in the mutated codon (MC) and/or the type of mutation produced.

These two steps are included to ensure that the TSM profiling method is able to identify different isoforms of DBDs, and to indicate the likely optimum length of highly specific target motifs defining the binding domains of any one isoform.

Example 2

TSM Profiles Indicate AID/APOBEC3G/APOBEC3B and ADAR1 Deaminase Activity

A TSM profile for the selected motifs for AID (WRCG/CGYW, where W=A/T; Y=T/C; and R=A/G), APOBEC3G (CCG/CGG), APOBEC3B (TCG/CGA) and ADAR1 (WAY, where W=A/T; and Y=T/C) is shown in Table 5. The Chi Square level of statistical significance for deviation from the expected is shown for mutations off each motif in a 3×3 dataset. All 3×3 datasets show a strong preference for mutations of a particular type, and at a preferred target location for significant level p<0.001 (8 df). It is important to note that although isoforms of the DBDs are known to exist for each deaminase, motifs for the dominant DBDs of each deaminase have been selected to ensure that there is no overlap among the selected deaminases.

TABLE 5

Identified C-PAS and Codon Context

| Deaminase family | Key motif | Mutation type | Mutated codon target site (5' to 3') | | | P-value |
|---|---|---|---|---|---|---|
| | | | MC-1 | MC-2 | MC-3 | |
| AID | WRCG | C to A | 7 | 17 | 17 | 1.54E−97 |
| | | C to G | 17 | 16 | 34 | |
| | | C to T | 138 | 59 | 141 | |
| | CGYW | G to A | 58 | 150 | 69 | 2.60E−93 |
| | | G to C | 7 | 16 | 21 | |
| | | G to T | 11 | 15 | 13 | |
| APOBEC3G | CCG | C to A | 20 | 10 | 20 | 1.52E−110 |
| | | C to G | 26 | 12 | 23 | |
| | | C to T | 172 | 69 | 130 | |
| APOBEC3B | CGG | G > A | 88 | 142 | 136 | 3.58E−88 |
| | | G > C | 22 | 27 | 16 | |
| | | G to T | 18 | 16 | 24 | |
| | TCG | C to A | 17 | 3 | 28 | 177E−48 |
| | | C to G | 26 | 12 | 11 | |
| | | C to T | 90 | 42 | 83 | |
| | CGA | G to A | 135 | 81 | 44 | 3.14E−82 |
| | | G to C | 16 | 12 | 7 | |
| | | G to T | 27 | 18 | 7 | |
| ADAR1 | WAY | A to C | 27 | 58 | 21 | 4.46E−61 |
| | | A to G | 110 | 191 | 71 | |
| | | A to T | 59 | 81 | 47 | |

The data in Table 5 reveal highly significant codon-bias patterns that have not previously been reported for serous ovarian adenocarcinoma samples. In each case, the observed deviation from the null hypothesis is highly significant. For AID and APOBEC3G motifs, the statistically significant MC-1 bias for cytidine deamination on the NTS results in a dominant number of C to T transitions, and the MC-2 bias for cytidine deamination on the TS results in a dominant number of G to A transitions. For the trinucleotide ADAR motif WAY, the dominant type of mutations are G to A transitions preferentially targeting MC-2 sites. These somatic mutation targets are consistent with a previous study of TP53 gene mutations for pooled breast cancer mutation data (see, Lindley, 2013).

Furthermore, FIG. 1 provides a graphical representation of the increase in the targeting specificity of motifs for the catalytic domain of AID as the number of nucleotides is incrementally increased from three nucleotides to six nucleotides. The graph of FIG. 1A shows how the relative number of background mutations decreases as the targeting preference of each motif is increased. The number of G to A mutations occurring at MC-2 sites is increased from 52% of all mutations of guanosine for the trinucleotide motif GYW, and increasing to 91% of all mutations of guanosine for the six nucleotide motif SCGYWW. A table showing the 3×3 TSM mutation distribution for the range of possible mutations of guanosine (G to A/C/T), and the target sites within the structure of the MC are included (see, FIG. 1B). The Chi Square level of statistical significance for deviation from the expected is shown for mutations off each motif for significance level p<0.001 (8 df).

The main conclusion drawn from these data is that the targeting preferences for AID binding domains are best defined by motifs of four or more nucleotides. That is, the biochemical binding mechanisms targeting sites for mutation are highly specific, and they involve more nucleotides than previous studies suggest. This example using the well known trinucleotide motif for AID as a starting point, also validates the use of TSM profiling as a useful approach for characterizing the variant isomorphic nature of the possible range of targeting preferences in other deaminases. Thus, the TSM methodology also provides a useful conceptual tool to test new predictions about the nature of the underlying three dimensional bio-molecular interactions involved in deamination.

Example 3

Different Isoforms of DBDs Result in Target Site Discrimination

To verify that different isoforms of ADAR DBDs may result in a shift in targeting preferences, the targeting preferences of a range of ADAR motifs with a W<u>A</u> or <u>A</u>W base composition were identified and compared. We also identified a shift in the location of the preferred target nucleotide position within the MC nucleotide structure for possible isoforms of AID deaminase domains using the trinucleotide base motifs W<u>R</u>C/<u>G</u>YW. The results are shown in Table 6. The Chi Square level of statistical significance for deviation from the expected is shown for mutations off each motif in a 3×3 dataset for significance level p<0.001 (8 df).

TABLE 6

Identified C-PAS and Codon Context

| Deaminase enzyme | Motif | Preferred mutation | Target codon position | p-value |
|---|---|---|---|---|
| ADARs | RAWA | A to T | MC-1 | 1.37E-01 |
|  | CWA | A to G | MC-2 | 5.21E-55 |
|  | GWA | A to G | MC-3 | 9.02E-17 |
|  | A WA | A to G | MC-1 | 6.10E-17 |
|  | A WG | A to G | MC-2 | 1.91E-47 |
|  | A WT | A to G | MC-3 | 3.44E-05 |
| AID | WRC GS | C to T | MC-1 | 5.00E-67 |
|  | XWRC T | C to T | MC-1 | 5.63E-09 |
|  | WRC AW | C to T | MC-3 | 2.90E-12 |
|  | WGG YW | G to T | MC-1 | 4.77E-08 |
|  | SCG YW | G to A | MC-2 | 1.13E-91 |
|  | STG YW | G to A | MC-3 | 4.83E-15 |

Referring to Table 6, it can be seen that the somatic targeting preferences for different DBDs may result in either a change in the dominant type of mutation produced, or a shift in the preferred target sites within the MC nucleotide structure, or both of these.

Using serous ovarian adenocarcinoma samples as an example, Table 6 illustrates a dominant TSM pattern resulting in A to G mutations at MC-2 sites for ADAR deaminase activity off the CW<u>A</u> motif (p=5.21E-55; 8 df) is observed. Similarly there is a dominant number of G to A mutations at MC-2 sites for AID deaminase activity off the SC<u>G</u>YW motif (p=1.13E-91; 8 df). In the case of the DBD isoforms off the <u>G</u>YW motifs associated with AID deaminase activity, SC<u>G</u>YW results in a dominant number of G to A mutations targeting MC-2 sites (p=1.13E-91, 8 df). However, by introducing a single nucleotide change of C to A, the SA<u>G</u>YW motif results in a dominant number of G to C mutations targeting MC-3 sites (p=6.13E-05, 8 df). Similarly, by introducing a single nucleotide change of C to G, the WG<u>G</u>YW motif results in a dominant number of G to T mutations targeting MC-1 sites (p=4.77E-08, 8 df). Other changes to nuclear context also demonstrate that target site discrimination for mutation type and/or the target site within the MC are produced. It is concluded that the TSM method can be used to identify the different targeting preferences of the possible isoforms defining the catalytic binding domains of a single deaminase.

This data clearly shows that selection and switching mechanisms play a role in deaminase target site selection in somatic tissue, and the initiation of the SHM-like changes are involved in oncogenic processes. This means that the TSM methods described here can be used to characterize differences in DBDs during oncogenesis, and to identify their effect on both the target site preferences and type of mutations produced. Accordingly, we sought to use the serous ovarian adenocarcinoma data as a training dataset to identify specific DBDs may be associated with disease progression.

Example 4

Identifying C-PAS and their Use in Predicting Recurrence/Prognosis

Using the TSM method, we identified several DBDs that are associated with disease progression indicators in serous ovarian adenocarcinoma samples. These DBDs met the key selection criteria described above (cf. Example 1), and subsequently designated here as Cancer-Progression Associated Signatures (C-PAS). The C-PAS identified herein are defined by the nucleotide sequence of their respective motifs thus identifying the specific deaminase binding site responsible for introducing the de novo mutation. The disease progression indicators for which clinical information is available include disease stage, and disease-free survival time. Table 7 shows the deaminase target motifs associated with AID, APOBEC3G, APOBEC3B and ADAR deaminase activity that are found to be associated with these cancer progression indicators. Each of these deaminases are ubiquitous in that they are known to play a role in oncogenesis, and they are found in all (or almost all) somatic tissue types.

Referring to Table 7, for the cohort of living patients that have had no recurrence of disease in the 60 months from the time of initial diagnosis, the average number of mutations off C-PAS per sample is 0.50. For the cohort of patients that have had a recurrence within 60 months from initial diagnosis, the average number of mutations per sample is increased more than three-fold to 1.87. In comparing the average number of C-PAS mutations per sample for each cohort, the Pearson product moment correlation (r) is 0.68 (significant at the p<0.001 level). These data suggest that the C-PAS are able to be used to determine the probability of recurrence of disease within five years after the initial diagnosis.

TABLE 7

C-PAS against Recurrence and Prognosis

| | Cancer-Progression Associated Signature (C-PAS) | | | | Number of mutations by progression status | | Number of mutations by stage | | |
|---|---|---|---|---|---|---|---|---|---|
| | | | | | Living & Disease | | | | |
| Type of deaminase | Target Motif | Mutation Type | Codon Site | Target site p-value | Free >60 mths (n = 10) | Recurred <60 mths (n = 100) | Stage IIA-IIIB (n = 22) | Stage IIIC (n = 142) | Stage IV (n = 30) |
| AID | WRCGSS | C to T | MC-1 | 5.2E-39 | 0 | 12 | 5 | 35 | 5 |
| APOBEC3B | TCGA | C to T | MC-1 | 5.8E-12 | 1 | 7 | 8 | 13 | 4 |
|  | ATCS | C to T | MC-3 | 9.8E-26 | 0 | 11 | 6 | 51 | 6 |

TABLE 7-continued

C-PAS against Recurrence and Prognosis

| | | | | | Number of mutations by progression status | | Number of mutations by stage | | |
|---|---|---|---|---|---|---|---|---|---|
| | Cancer-Progression Associated Signature (C-PAS) | | | | Living & Disease | | | | |
| Type of deaminase | Target Motif | Mutation Type | Codon Site | Target site p-value | Free >60 mths (n = 10) | Recurred <60 mths (n = 100) | Stage IIA-IIIB (n = 22) | Stage IIIC (n = 142) | Stage IV (n = 30) |
| APOBEC3G | GCGGC | C to T | MC-1 | 1.1E−25 | 0 | 7 | 1 | 26 | 3 |
| | CCGX | C to T | MC-1 | 1.8E−57 | 2 | 24 | 9 | 72 | 11 |
| | ZCCG | C to T | MC-1 | 2.6E−71 | 2 | 27 | 6 | 77 | 17 |
| | SGGRR | G to A | MC-1 | 1.6E−31 | 0 | 9 | 3 | 45 | 8 |
| | TCCG | C to T | MC-1 | 3.3E−45 | 0 | 4 | 3 | 29 | 5 |
| | GCGC | G to A | MC-2 | 2.6E−44 | 0 | 11 | 2 | 51 | 6 |
| | CCGGC | G to A | MC-2 | 5.6E−11 | 0 | 6 | 4 | 9 | 3 |
| ADARs | RAA | A to T | MC-1 | 1.4E−09 | 0 | 9 | 6 | 29 | 11 |
| | WAW | A to G | MC-1 | 1.6E−09 | 0 | 8 | 2 | 24 | 4 |
| | SARA | A to G | MC-1 | 1.5E−13 | 0 | 17 | 2 | 51 | 3 |
| | TWTY | T to C | MC-2 | 1.1E−10 | 0 | 16 | 8 | 47 | 5 |
| | TWTY | T to C | MC-3 | 1.1E−10 | 0 | 19 | 4 | 27 | 5 |
| | Total number of mutations | | | | 5 | 187 | 69 | 586 | 96 |
| | Average number of mutations per sample | | | | 0.5 | 1.87 | 3.1 | 4.1 | 3.2 |

When the average number of mutations per sample is compared by cancer or tumour stage, it is found that the average number of mutations per sample for stages IIA-IIIB is 3.1. The average number of mutations of the identified C-PAS per sample for stage IIIC is 4.1, and 3.2 for stage IV. In comparing the average number of mutations per sample for stages IIA-IIIB compared to stage IIIC, the Pearson product moment correlation r is 0.28 (not significant at the p n<0.05 level). However, when the average number of mutations per sample for stage IIIC is compared to stage IV samples, the Pearson product moment correlation r is 0.69 (significant at the p<0.001 level).

Unexpectedly, the average number of mutations from the set of C-PAS included in this study is significantly less for stage IV in comparison to stage IIIC samples. The decrease might be explained by the tissue sampling methods used to call single nucleotide variants (SNV). The somatic genomic variations in apparently normal or healthy tissue can impact oncogenesis, although how this occurs is poorly understood. Tomasetti et al. (2013) have suggested that half or more of the single point mutations in cancers could have arisen prior to the development of a tumour. Recently, Martincorena et al (2015) have found that more than a quarter of the apparently healthy human epidermal skin cells harbour cancer-causing somatic mutations. Once TSM processes become active in apparently normal tissue, then it is likely that individual somatic cells in a tissue will harbor a diverse range of genetic changes. Apparently healthy tissue in late stage IV cancer may harbour many of the mutations associated with the C-PAS identified in stage IIIC. Thus, the tissue matching methods used by the TCGA to call SNV may exclude those variants identified in both samples. This means that many of the mutations associated with C-PAS may be excluded from the mutation datasets produced, and may partly explain the decrease. However, in general terms these results and their significance support the concept that a SHM-like 'switching mechanism' may be activated in late stage IIIC cancers, and trigger the production of new DBDs.

From the results in Table 6, the identified C-PAS were used to explore their efficacy in a prognostic assay to predict which patients are likely to have a recurrence or progression of disease. Although there are some limitations in the methods used to call the SNV, the training data set of C-PAS was used as a 'first pass' reference test to attempt to differentiate between those patients that will develop a recurrence with five years of the initial diagnosis from those that will not.

The number of mutations occurring at motifs for each of the identified C-PAS was tabulated for each sample. A negative test result was recorded if no mutations occurred at any of the identified C-PAS, and as positive if there was one or more. The mutation data and the test result for each sample is not provided.

Figure 2:
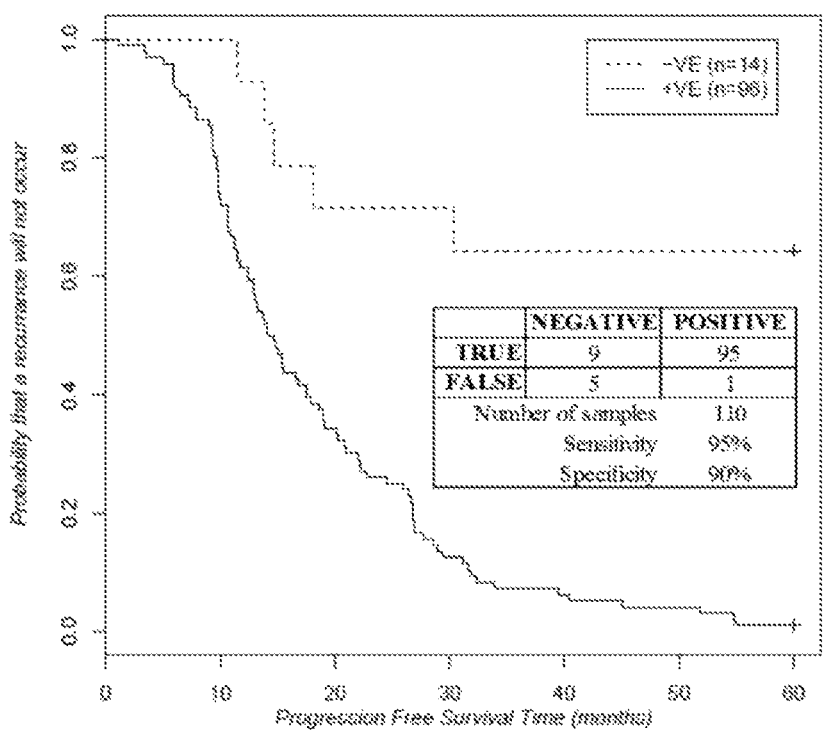
FIG. 2 provides a Kaplan-Meier plot predicting survival probabilities for 110 high grade serous ovarian adenocarcinoma samples with positive or negative cancer-progression association signature (C-PAS) test result.

FIG. 2 shows a Kaplan-Meier plot predicting disease-free survival times for high-grade serous ovarian adenocarcinoma samples with a positive test outcome, and compared to those with a negative test result. The difference between the two cohorts by test result is highly significant. The Cox P-value is 1.57E-05, and the Log-Rank P value is 7.86E-07. Also included in FIG. 2 are the sensitivity and specificity measures. Data collected in respect of 52 samples that had a recorded progression free survival time of less than 60 months at the time of their last visit, 31 samples with progression-free survival data missing, and one sample from an individual that was deceased with the cause of death unknown were removed from these analyses. Referring to FIG. 2, only 12% of patients with a positive test result did not have a recurrence of disease after 30 months. After 60 months, only one patient of the 96 with a positive test result did not have a recurrence of disease. The results demonstrate the potential clinical utility of the TSM profiling approach in predicting the probability of recurrence of disease. Referring to the sensitivity and specificity measures for the test shown in FIG. 2, the sensitivity measure is 95%, and the specificity is 90%.

This example demonstrates that DBD isoforms involving one or more nucleotide changes will result in target site discrimination, and that the resulting transformations can be used to identify new DBD isoforms arising during oncogenesis. It also demonstrates that the C-PAS identified provides the basis for the development of novel genetic tests to predict the likelihood of disease progression. The method disclosed in this example presents us with a fundamentally new genomic analysis toolkit for identifying some important differences in isomorphic forms of DBDs arising in an individual during oncogenesis. TSM profiling can be used to provide important information for the diagnosis of disease associated with aberrant deaminase activity.

Example 5

Identifying C-PAS in Acute Myeloid Leukaemia (AML)

To provide further proof of concept examples of the application of the present invention, samples from a cancer sample affecting a different tissue type (namely, acute myeloid leukaemia (AML)) was assessed for clinically relevant C-PAS. Table 8 provides a summary of the number of samples for which clinical records and matched sequence data are publically provided.

TABLE 8

Clinical Data on Alternative Cancer Samples

| Cancer type | Tumour Free | Recurred/ Progressed | Total Used | Total Samples |
|---|---|---|---|---|
| Ovarian | 10 | 100 | 110 | 197 |
| AML | 16 | 86 | 102 | 103 |

Single nucleotide variant (mutation) information in VCF format is extracted from TCGA mutation files. Other variants such as insertion/deletions or structural variants ignored. The samples meeting the group selection criteria were analysed using a proprietary online Codon Reference Information System (or the 'CRIS' processor). Using genomic coordinates of the .vcf data file the exon context of SNV was determine. If the SNV is three base pairs or more inside an ENSEMBL hg38 coding sequence (cds) of an exon, then the strand and phase of the coding sequence is reported. The codon context of SNV within the region defined by three base pairs of the intron/exon boundary regions was analysed to avoid the ambiguity of binding motifs. If more than one exon is identified, then the exon in order of the canonical transcript is chosen.

A nine-base genomic window is analysed around the SNV position to identify the bases either side of the SNV within the three nucleotide structure of each codon. The complete three codons are the mutated codon (MC) containing the mutation in either the first, second or third nucleotide position read 5-prime (5') to 3-prime (3') and annotated as MC-1, MC-2 and MC-3 respectively, the 5' and 3' codons either side of the mutated codon. If the SNV is located on a gene on the negative strand, then the reverse complement of the three codons is extracted.

The CRIS processor was used to conduct motif searches for the main target motifs known to be associated with the DNA/RNA targeting preferences of deaminases (e.g., AID (WRC/GYW), ADAR1 (WA/TW), APOBEC3G (CC/GG) and APOBEC3B (TCA/TGA)). Standard and non-overlapping motifs extending to 4-5 nts are also used to search for the AID, ADAR1, APOBEC3G and APOBEC3B motifs for SNV. Results are tabulated for each codon and each type of mutation.

More specifically, this example discloses representative in silico methods of mutation data analysis to: (i) identify the likely source of mutations arising during oncogenesis in acute myeloid leukaemia (AML); and (ii) to identify new mutation signatures for predicting progression-free survival. As described in detail above, the new C-PAS identified for predicting progression-free survival are present in significantly higher numbers in the cohort of patients whose disease did progress or recur within a period of less than 60 months from the time of the initial diagnosis. That is, the new mutation signatures identified and used as a basis for assay development in this example are those APOBEC/ADAR DBD homologues that are determinative of negative prediction for survival over 60 months. A subset of C-PAS is used as a test to differentiate between those patients whose disease progresses (or recurs) within 60 months from those that remain disease free.

In this example, a method to use a subset of C-PAS identified to develop an assay predicting the likelihood of cancer recurrence is described. The clinical information used for this study was obtained from the cBioPortal web site (www.cbioportal.org/data_sets.jsp; accessed on 20 Dec. 2015) by querying a single cancer study. The TCGA AML (see, TCGA, New Eng. J. Med. Res., 2013) was selected. In this study, the genomes of 200 clinically annotated adult cases of de novo AML, using either whole-genome sequencing (50 cases) or whole-exome sequencing (150 cases), along with RNA and microRNA sequencing and DNA-methylation analysis, were analysed. The TCGA Sample and Patient ID, the corresponding COSMIC .vcf mutation data files for each patient were accessed and downloaded on 4-8 Feb. 2016.

The selection criteria for a subset of samples was selected for inclusion in this study using the following selection criteria: (i) the availability of a clinical data sheet that includes: a TCGA identifier, disease status at last visit, survival status (living/deceased), disease free status (disease free/recurred or progressed) and disease free months; and (ii) the availability of a COSMIC .vcf mutation data file with matching TCGA identifier. Clinical data can also be used to include patients in either of the following two cohorts: those patients that remained disease-free for more than 60 months and "living;" and those patients in which the cancer recurred and/or progressed in 60 months or less.

Table 9 shows the identification of the C-PAS identified from the AML mutation dataset using the previously described method. In this example, the number of patients having at least one or more of the C-PAS mutation, rather than the number of mutations from each of the cohorts compared is shown. C-PAS are indicated by mutation type, the target motif and its codon context where MC1-3 indicates the location of the mutated nucleotide (read 5-prime to 3-prime).

TABLE 9

Tabulated results showing number of mutations for each C-PAS

| Deaminase Family | Mutation Type | Target motif | Target site | Living/ Disease Free >60 months (n = 16) | Recurred/ Progressed <60 months (n = 86) |
|---|---|---|---|---|---|
| APOBECs | C > T | CCZ | MC-1 | 0 | 20 |
|  | C > T | SWCS | MC-2 | 0 | 22 |
|  | G > A | XNGNS | MC-3 | 0 | 23 |
|  | G > A | GSA | MC-2 | 0 | 21 |
|  | G > A | SGXW | MC-1 | 0 | 23 |
|  | G > A | CXGS | MC-3 | 0 | 22 |
|  | G > A | YXGNX | MC-3 | 0 | 24 |

TABLE 9-continued

Tabulated results showing number of mutations for each C-PAS

| Deaminase Family | Mutation Type | Target motif | Target site | Living/ Disease Free >60 months (n = 16) | Recurred/ Progressed <60 months (n = 86) |
|---|---|---|---|---|---|
| | G > A | YYGNX | MC-3 | 0 | 23 |
| | G > A | WNGNZ | MC-1 | 0 | 20 |
| | | Total | | 0 | 70 |
| | | Average per sample | | 0 | 4.213 |

Table 9 shows the tabulated results for a subset of samples indicating the total number of mutations for each of the C-PAS found for each sample. The selected panel of C-PAS is used to develop a predictive test for the prediction of the recurrence or progression of AML within a 60 month timeframe. A test result is considered to give a positive result if there are mutations at sites indicating a C-PAS that is associated with progression or recurrence of disease. That is, a positive test result indicates a high likelihood that the disease will recur and/or progress within 60 months. A negative test result is reported if it is found that there are no mutations (or equal or less than what would be expected if the mutations occurred at random) found at sites known to be associated with cancer progression and/or recurrence.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Bass, RNA editing by adenosine deaminases that act on RNA, Ann. Rev. Biochem., 71: 817-846. 2002

Basu, U., Meng, F. L., Keim, C., Grinstein, V., Pefanis, E., Eccleston, J., Zhang, T., Myers, D., Wasserman, C. R., Wesemann, D. R., Januszyk, K., Gregory, R. I., Deng, H., Lima, C. D., The RNA exosome targets the AID cytidine deaminase to both strands of transcribed duplex DNA substrates, Cell, 2011, 144(3): 353-63.

Beale, R. C., Petersen-Mahrt, S. K., Watt, I. N., Harris, R. S., Rada, C., Neuberger, M. S., Comparison of the differential context-dependence of DNA deamination by APOBEC enzymes: correlation with mutation spectra in vivo, J. Mol. Biol., 2004, 337(3): 585-96.

Burns, M. B., Lackey, L., Carpenter, M. A., Rathore, A., Land, A. M., Leonard, B., Refsland, E. W., Kotandeniya, D., Tretyakova, N., Nikas, J. B., Yee, D., Temiz, N. A., Donohue, D. E., McDougle, R. M., Brown, W. L., Law, E. K., Harris, R. S., APOBEC3B is an enzymatic source of mutation in breast cancer, Nature, 2013, 494(7437): 366-70.

Burns, M. B., Temiz, N. A., Harris, R. S., Evidence for APOBEC3B mutagenesis in multiple human cancers, Nat Genet., 2013, 45(9): 977-83.

Chan, T. H., Lin, C. H., Qi, L., Fei, J., Li, Y., Yong, K. J., Liu, M., Song, Y., Chow, R. K., Ng, V. H., Yuan, Y. F., Tenen, D. G., Guan, X. Y., Chen, L., A disrupted RNA editing balance mediated by ADARs (Adenosine DeAminases that act on RNA) in human hepatocellular carcinoma, 2014, Gut, 63(5): 832-43.

Contilcello, S. G., The AID/APOBEC family of nucleic acid mutators, Genome Biol., 2008; 9(6): 229.

Cunningham, F. M., Amode, R., Barrell, D., Beal, K., Billis, K., et al., Nucleic Acids Research, 43: Database issue: D662-D669.

Farajollahi, S., and Maas, S., 2010 Molecular diversity through RNA editing: a balancing act, Trends Genet, 2010, 26(5): 221-30.

Gallo, A., Galardi, S., A-to-I RNA editing and cancer: from pathology to basic science, RNA Biol., 2008, 5(3): 135-9.

George, C. X., Samuel, C. E., Human RNA-specific adenosine deaminase ADAR1 transcripts possess alternative exon 1 structures that initiate from different promoters, one constitutively active and the other interferon inducible, Proc. Natl. Acad. Sci. USA., 1999, 96(8): 4621-6.

George, C. X., Wagner, M. V., Samuel, C. E., Expression of interferon-inducible RNA adenosine deaminase ADAR1 during pathogen infection and mouse embryo development involves tissue-selective promoter utilization and alternative splicing, J. Biol. Chem., 2005, 280(15): 15020-8.

Honjo, T., Kobayashi, M., Begum, N., Kotani, A., Sabouri, S., Nagaoka, H., The AID dilemma: infection, or cancer? Adv. Cancer Res., 2012, 113: 1-44.

Howlader, N., Noone, A. M., Krapcho, M., Garshell, J., Miller, D., Altekruse, S. F., Kosary, C. L. et al., SEER Cancer Statistics Review, 1975-2010, National Cancer Institute, Bethesda, Md. http://seer.cancer.gov/csr, Posted to SEER website April 2013.

Kanchi, K. L., Johnson, K. J., Lu, C., McLellan, M. D., Leiserson, M. D., Wendl, M. C., Zhang, Q., Koboldt, D. C., Xie, M., Kandoth, C., McMichael, J. F., Wyczalkowski, M. A., Larson, D. E., Schmidt, H. K., Miller, C. A., Fulton, R. S., Spellman, P. T., Mardis, E. R., Druley, T. E., Graubert, T. A., Goodfellow, P. J., Raphael, B. J., Wilson, R. K., Ding, L., Integrated analysis of germline and somatic variants in ovarian cancer, Nat. Commun., 2014, 5: 3156.

Leonard, B., Hart, S. N., Burns, M. B., Carpenter, M. A., Temiz, N. A., Rathore, A., Vogel, R. I., Nikas, J. B., Law, E. K., Brown, W. L., Li, Y., Zhang, Y., Maurer, M. J., Oberg, A. L., Cunningham, J. M., Shridhar, V., Bell, D. A., April, C., Bentley, D., Bibikova, M., Cheetham, R. K., Fan, J. B., Grocock, R., Humphray, S., Kingsbury, Z., Peden, J., Chien, J., Swisher, E. M., Hartmann, L. C., Kalli, K. R., Goode, E. L., Sicotte, H., Kaufmann, S. H., Harris, R. S., APOBEC3B upregulation and genomic mutation patterns in serous ovarian carcinoma, Cancer Res., 2013, 73(24): 7222-31.

Lindley, R. A., The importance of codon context for understanding the Ig-like somatic hypermutation strand-biased patterns in TP53 mutations in breast cancer. Cancer Genet. 2013, 206(6): 222-6.

Lindley, R. A., and Steele, E. J., Critical Analysis of Strand-Biased Somatic Mutation Signatures in TP53 versus Ig Genes, in Genome-Wide Data and the Etiology of Cancer, Review Article, ISRN Genomics 2013, 1-18.

Martincorena, I., Roshan, A., Gerstung, M., Ellis, P., Van Loo, P., McLaren, S. et al., High burden and pervasive positive selection of somatic mutations in normal human skin, *Science*, 348(6237): 880-886.

Maul, R. W., Gearhart, P. J., AID and somatic hypermutation *Adv. Immunol.*, 2010, 105: 159-91.

Miller, D. S., Blessing, J. A., Krasner, C. N., Mannel, R. S., Hanjani, P., Pearl, M. L., Waggoner S E, Boardman C H. Phase II evaluation of pemetrexed in the treatment of recurrent or persistent platinum-resistant ovarian or primary peritoneal carcinoma: a study of the Gynecologic Oncology Group, *J. Clin. Oncol.*, 2009, 27(16): 2686-91.

Nabel, C. S., Jia, H., Ye, Y., Shen, L., Goldschmidt, H. L., Stivers, J. T., Zhang, Y., Kohli, R. M., AID/APOBEC deaminases disfavor modified cytosines implicated in DNA demethylation, *Nat. Chem. Biol.*, 2012, 8(9): 751-8.

Okazaki, I. M., Hiai, H., Kakazu, N., Yamada, S., Muramatsu, M., Kinoshita, K., Honjo, T. Constitutive expression of AID leads to tumourigenesis, *J. Exp. Med.*, 2003, 197(9): 1173-81.

Pauklin, S., Sernandez, I. V., Bachmann, G., Ramiro, A. R., Petersen-Mahrt, S. K., Estrogen directly activates AID transcription and function, *J Exp Med.*, 2009, 206(1): 99-111.

Paz, N., Levanon, E. Y., Amariglio, N., Heimberger, A. B., Ram, Z., Constantini, S., Barbash, Z. S., Adamsky, K., Safran, M., Hirschberg, A., Krupsky, M., Ben-Dov, I., Cazacu, S., Mikkelsen, T., Brodie, C., Eisenberg, E., Rechavi, G., Altered adenosine-to-inosine RNA editing in human cancer, *Genome Res.*, 2007, 17(11): 1586-95.

Rausch, J. W., Chelico, L., Goodman, M. F., Le Grice, S. F., Dissecting APOBEC3G substrate specificity by nucleoside analog interference, *J. Biol. Chem.*, 2009, 284(11): 7047-58.

Roberts, S. A., Lawrence, M. S., Klimczak, L. J., Grimm, S. A., Fargo, D., Stojanov, P., Kiezun, A., Kryukov, G. V., Carter, S. L., Saksena, G., Harris, S., Shah, R. R., Resnick, M. A., Getz, G., Gordenin, D. A., An APOBEC cytidine deaminase mutagenesis pattern is widespread in human cancers, *Nat. Genet.*, 2013, 45(9): 970-6.

Sasaki, H., Suzuki, A., Tatematsu, T., Shitara, M., Hikosaka, Y., Okuda, K., Moriyama, S., Yano, M., Fujii, Y., APOBEC3B gene overexpression in non-small-cell lung cancer, *Biomed. Rep.*, 2014, 2(3): 392-395.

Sheehy, A. M., Gaddis, N.C., Choi, J. D., Malim, M. H., Isolation of a human gene that inhibits HIV-1 infection and is suppressed by the viral Vif protein, *Nature*, 2002, 418(6898): 646-50.

Steele, E. J., Lindley, R. A., Somatic mutation patterns in non-lymphoid cancers resemble the strand biased somatic hypermutation spectra of antibody genes, *DNA Repair (Amst)*, 2010, 9(6): 600-3.

Tomasetti C., Vogelstein B., Parmigiani G., Half or more of the somatic mutations in cancers of self-renewing tissues originate prior to tumour initiation, *Proc. Natl. Acad. Sci. USA.*, 2013.

What is claimed is:

1. A method of treating or preventing a cancer in a subject, the method comprising
   (i) determining the likelihood that a cancer will recur in a subject, wherein the determination is made by a) analyzing the sequence of a nucleic acid molecule in a biological sample obtained from the subject to determine for a plurality of mutations of a mutation type at one or more motifs recognized or targeted by a mutagenic agent the codon context of those mutations to thereby identify the location of a mutation and mutation type for each of a plurality of mutated codons in the nucleic acid molecule, wherein the codon context of an individual mutation is determined by determining at which of the three positions of a corresponding mutated codon the individual mutation occurs; and (b) determining that the cancer is likely to recur in the subject when a level of mutation of a mutation type at one of the three positions in the plurality of mutated codons is above a predetermined threshold that correlates with the recurrence of the cancer; and
   (ii) exposing the subject to a therapy on the basis that the cancer is determined as likely to recur in the subject, wherein:
   (a) the cancer is ovarian cancer, and the biological sample contains ovarian tissue or cells, and wherein:
   a determination that cancer recurrence is likely when the level of C to T mutations in WRCGSS motifs at the first position of mutated codons (MC-1 sites) of the nucleic acid molecule is above a predetermined threshold;
   a determination that cancer recurrence is likely is made when the level of C to T mutations in TCGA motifs at MC-1 sites of the nucleic acid molecule is above a predetermined threshold;
   a determination that cancer recurrence is likely is made when the level of C to T mutations in ATCS motifs at the third position of mutated codons (MC-3 sites) of the nucleic acid molecule is above a predetermined threshold;
   a determination that cancer recurrence is likely is made when the level of C to T mutations in GCGGC motifs at MC-1 sites of the nucleic acid molecule is above a predetermined threshold;
   a determination that cancer recurrence is likely is made when the level of G to A mutations in SGGRR motifs at MC-1 sites of the nucleic acid molecule is above a predetermined threshold;
   a determination that cancer recurrence is likely is made when the level of C to T mutations in TCCG motifs at MC-1 sites of the nucleic acid molecule is above a predetermined threshold;
   a determination that cancer recurrence is likely is made when the level of G to A mutations in GCGC motifs at the second position of mutated codons (MC-2 sites) of the nucleic acid molecule is above a predetermined threshold;
   a determination that cancer recurrence is likely is made when the level of G to A mutations in CCGGC motifs at MC-2 sites of the nucleic acid molecule is above a predetermined threshold;
   a determination that cancer recurrence is likely is made when the level of A to T mutations in RAWA motifs at MC-1 sites of the nucleic acid molecule is above a predetermined threshold;
   a determination that cancer recurrence is likely is made when the level of A to G mutations in WTAW motifs at MC-1 sites of the nucleic acid molecule is above a predetermined threshold;
   a determination that cancer recurrence is likely is made when the level of A to G mutations in SARA motifs at MC-1 sites of the nucleic acid molecule is above a predetermined threshold;
   a determination that cancer recurrence is likely is made when the level of T to C mutations in TWTY motifs at MC-2 sites of the nucleic acid molecule is above a predetermined threshold; or a determination that cancer recurrence is likely is made when the level of T to C mutations in TWTY motifs at MC-3 sites of the nucleic acid molecule is above a predetermined threshold;

and wherein the therapy is selected from the group consisting of radiotherapy, surgery, chemotherapy, and immunotherapy; or (b) the cancer is acute myeloid leukemia (AML) and the biological sample contains hematopoietic tissue or cells, wherein:

a determination that cancer recurrence is likely is made when the level of C to T mutations in SWCS motifs at MC-2 sites of nucleic acid molecule from a biological sample is above a predetermined threshold; or a determination that cancer recurrence is likely is made when the level of G to A mutations in GSA motifs at MC-2 sites of the nucleic acid molecule from a biological sample is above a predetermined threshold, and wherein the therapy is selected from the group consisting of radiotherapy, surgery, chemotherapy, and immunotherapy; and wherein the underlined nucleotide in each motif is the mutated nucleotide.

2. The method according to claim 1, wherein the biological sample having greater than 1.87 mutations means it is likely that the cancer or tumor will recur.

3. The method according to claim 2, wherein the recurrence will likely occur within 60 months.

* * * * *